US011147444B2

(12) United States Patent
Vella et al.

(10) Patent No.: US 11,147,444 B2
(45) Date of Patent: Oct. 19, 2021

(54) SPECULUM WITH SECONDARY BILLS

(71) Applicant: CEEK Women's Health, Inc., Portland, OR (US)

(72) Inventors: Ethan Vella, Portland, OR (US); Fahti Self, Portland, OR (US); Maria Lalli, Portland, OR (US); Darius Naigamwalla, Portland, OR (US); Chase Thompson, Portland, OR (US)

(73) Assignee: CEEK Women's Health, Inc., Portland, OR (US)

( * ) Notice: Subject to any disclaimer, the term of this patent is extended or adjusted under 35 U.S.C. 154(b) by 311 days.

(21) Appl. No.: 15/392,988

(22) Filed: Dec. 28, 2016

(65) Prior Publication Data
US 2017/0181616 A1 Jun. 29, 2017

Related U.S. Application Data

(60) Provisional application No. 62/310,620, filed on Mar. 18, 2016, provisional application No. 62/310,597, (Continued)

(51) Int. Cl.
*A61B 1/32* (2006.01)
*A61B 1/04* (2006.01)
(Continued)

(52) U.S. Cl.
CPC ............ *A61B 1/32* (2013.01); *A61B 1/00066* (2013.01); *A61B 1/04* (2013.01); *A61B 1/06* (2013.01); *A61B 1/303* (2013.01); *A61M 29/00* (2013.01)

(58) Field of Classification Search
CPC ........... A61B 1/303; A61B 1/307; A61B 1/31; A61B 1/32; A61B 17/0293; A61B 17/0206; A61B 17/0218; A61B 17/02
(Continued)

(56) References Cited

U.S. PATENT DOCUMENTS

| 55,511 A | 6/1866 | Lentz |
| 977,489 A | 12/1910 | Von Unruh |

(Continued)

FOREIGN PATENT DOCUMENTS

| AU | 2016380985 A1 | 7/2018 |
| CN | 201595813 U | 10/2010 |

(Continued)

OTHER PUBLICATIONS

International Search Report and Written Opinion for Application No. PCT/US2016/069043, dated Jul. 7, 2017.
(Continued)

*Primary Examiner* — Amy R Sipp
(74) *Attorney, Agent, or Firm* — Mintz Levin Cohn Ferris Glovsky and Popeo, P.C.

(57) ABSTRACT

The disclosure relates to methods and apparatuses relating to a speculum. The speculum includes a handle, a first bill and a second bill, where a proximal end portion of the first bill and the second bill are coupled to an upper portion of the handle and configured to open along a first axis, a third bill and a fourth bill, where a proximal end portion of the third bill and the fourth bill are coupled to the upper portion of the handle and configured to open along a second axis substantially orthogonal to the first axis and an actuation mechanism that causes the first bill and the second bill to move between an open position and a closed position. In some embodiments, the speculum includes a locking mechanism with a rocker mechanism, a lock strip contained in a handle of the speculum, and a pawl coupled to the handle.

20 Claims, 18 Drawing Sheets

Related U.S. Application Data filed on Mar. 18, 2016, provisional application No. 62/281,699, filed on Jan. 21, 2016, provisional application No. 62/281,685, filed on Jan. 21, 2016, provisional application No. 62/272,625, filed on Dec. 29, 2015, provisional application No. 62/272,613, filed on Dec. 29, 2015.

(51) Int. Cl.
    *A61B 1/06*     (2006.01)
    *A61B 1/00*     (2006.01)
    *A61M 29/00*     (2006.01)
    *A61B 1/303*     (2006.01)

(58) Field of Classification Search
    USPC ......................................................... 600/220
    See application file for complete search history.

(56) References Cited

U.S. PATENT DOCUMENTS

| | | |
|---|---|---|
| 1,969,671 A | 8/1934 | Nelson |
| 2,083,573 A | 6/1937 | Morgan |
| 2,123,343 A | 7/1938 | Rightsell |
| 2,324,485 A | 7/1943 | Chamberlain |
| 2,509,241 A | 5/1950 | Mende |
| 2,579,849 A | 12/1951 | Newman |
| 2,670,736 A | 3/1954 | Dunkelberger |
| 2,714,886 A | 8/1955 | Castelli |
| 2,884,925 A | 5/1959 | Meynier |
| 2,954,025 A | 9/1960 | Grieshaber |
| 3,110,305 A | 11/1963 | Sygnator |
| 3,139,886 A | 7/1964 | Tallman |
| 3,246,646 A | 4/1966 | Murphy, Jr. |
| 3,324,850 A | 6/1967 | Gunning et al. |
| 3,332,414 A * | 7/1967 | Gasper ................ A61B 1/32 |
| | | 600/222 |
| 3,532,088 A | 10/1970 | Fiore |
| 3,565,061 A | 2/1971 | Reynolds |
| 3,650,266 A | 3/1972 | Pestka et al. |
| 3,744,481 A | 7/1973 | McDonald |
| 3,752,149 A | 8/1973 | Ungar et al. |
| 3,762,400 A | 10/1973 | McDonald |
| 3,769,968 A * | 11/1973 | Blount ................ A61B 1/32 |
| | | 600/223 |
| 3,815,585 A | 6/1974 | Fiore |
| 3,841,317 A | 10/1974 | Awais |
| 3,851,642 A | 12/1974 | McDonald |
| 3,857,395 A | 12/1974 | Johnson et al. |
| 3,885,563 A | 5/1975 | Johnson et al. |
| 3,890,961 A | 6/1975 | Moore |
| 4,004,591 A | 1/1977 | Freimark |
| 4,010,751 A | 3/1977 | Ring |
| 4,344,419 A | 8/1982 | Burgin |
| 4,356,817 A | 11/1982 | McKibben et al. |
| 4,428,370 A | 1/1984 | Keely |
| 4,492,220 A | 1/1985 | Hayes |
| 4,502,468 A | 3/1985 | Burgin |
| 4,566,439 A | 1/1986 | Burgin |
| 4,597,382 A | 7/1986 | Perez, Jr. |
| 4,638,792 A | 1/1987 | Burgin |
| 4,676,773 A | 6/1987 | Sheldon |
| 4,735,621 A | 4/1988 | Hessel |
| 4,805,604 A | 2/1989 | Spery |
| 4,807,600 A | 2/1989 | Hayes |
| 4,834,077 A | 5/1989 | Sun |
| 4,857,175 A | 8/1989 | Spinnler |
| 4,867,176 A | 9/1989 | Lash |
| 4,945,923 A | 8/1990 | Evans et al. |
| 4,976,273 A | 12/1990 | Hessel |
| 4,981,147 A | 1/1991 | Barnett |
| 4,984,564 A | 1/1991 | Yuen |
| 4,993,433 A | 2/1991 | Reddy |
| 5,007,409 A | 4/1991 | Pope |
| 5,041,080 A | 8/1991 | Shimatani et al. |
| 5,072,720 A | 12/1991 | Francis et al. |
| 5,083,414 A | 1/1992 | Wu |
| 5,094,250 A | 3/1992 | Hessel |
| 5,135,475 A | 8/1992 | Nakanishi et al. |
| 5,156,165 A | 10/1992 | Wu |
| 5,174,278 A | 12/1992 | Babkow |
| 5,179,936 A | 1/1993 | Ohara et al. |
| 5,179,937 A | 1/1993 | Lee |
| 5,193,555 A | 3/1993 | Richardson et al. |
| 5,209,241 A | 5/1993 | Hardy |
| 5,243,966 A | 9/1993 | Ng |
| 5,342,385 A | 8/1994 | Norelli et al. |
| 5,347,995 A | 9/1994 | Slater et al. |
| 5,377,667 A * | 1/1995 | Patton ................ A61B 1/32 |
| | | 600/184 |
| 5,433,219 A | 7/1995 | Spery |
| 5,460,165 A | 10/1995 | Mayes |
| 5,505,690 A | 4/1996 | Patton et al. |
| 5,540,658 A | 7/1996 | Evans et al. |
| 5,598,852 A | 2/1997 | Spery |
| 5,622,185 A | 4/1997 | Richardson et al. |
| 5,623,946 A | 4/1997 | Hessel |
| 5,687,741 A | 11/1997 | Torger |
| 5,716,329 A | 2/1998 | Dieter |
| 5,743,852 A | 4/1998 | Johnson |
| 5,785,648 A | 7/1998 | Min |
| 5,865,729 A | 2/1999 | Meehan et al. |
| 5,868,668 A | 2/1999 | Weiss |
| 5,992,415 A | 11/1999 | Alla et al. |
| 6,019,743 A | 2/2000 | Cole et al. |
| 6,024,696 A | 2/2000 | Hoftman et al. |
| 6,036,638 A | 3/2000 | Nwawka |
| 6,048,308 A | 4/2000 | Strong |
| 6,095,998 A | 8/2000 | Osborn, III et al. |
| 6,096,046 A | 8/2000 | Weiss |
| 6,174,282 B1 | 1/2001 | Tan |
| 6,186,973 B1 | 2/2001 | Buzot |
| 6,248,089 B1 | 6/2001 | Porat |
| 6,254,566 B1 | 7/2001 | Buck et al. |
| 6,280,379 B1 | 8/2001 | Resnick |
| 6,287,251 B1 | 9/2001 | Tan |
| 6,302,862 B1 | 10/2001 | Osborn, III et al. |
| 6,341,607 B1 | 1/2002 | Couvreur |
| 6,347,243 B1 | 2/2002 | Fraden |
| 6,354,995 B1 | 3/2002 | Hoftman et al. |
| 6,361,543 B1 | 3/2002 | Chin et al. |
| 6,379,299 B1 | 4/2002 | Borodulin et al. |
| 6,395,012 B1 | 5/2002 | Yoon et al. |
| 6,416,466 B1 | 7/2002 | Hsiao |
| 6,416,467 B1 | 7/2002 | McMillin |
| 6,428,474 B1 | 8/2002 | Weiss |
| 6,432,048 B1 | 8/2002 | Francois |
| 6,436,033 B2 | 8/2002 | Tan |
| 6,508,780 B1 | 1/2003 | Edgett et al. |
| D474,275 S | 5/2003 | Tan |
| 6,569,091 B2 | 5/2003 | Diokno et al. |
| 6,669,654 B2 | 12/2003 | Diokno et al. |
| 6,702,740 B2 | 3/2004 | Herold |
| 6,902,530 B1 | 6/2005 | Pianka |
| 6,939,289 B2 | 9/2005 | Zunker et al. |
| 7,047,975 B2 | 5/2006 | Austin et al. |
| 7,063,664 B2 | 6/2006 | Mohajer |
| 7,105,007 B2 | 9/2006 | Hibler |
| 7,172,573 B1 | 2/2007 | Lamb |
| 7,311,663 B2 | 12/2007 | Marcotte et al. |
| D558,871 S | 1/2008 | Osterberg |
| 7,322,358 B2 | 1/2008 | Tam et al. |
| 7,338,462 B2 | 3/2008 | Minoguchi et al. |
| 7,371,212 B2 | 5/2008 | Klaassen |
| 7,392,807 B2 | 7/2008 | Osterberg |
| D593,195 S | 5/2009 | Osterberg |
| 7,654,953 B2 | 2/2010 | Borodulin et al. |
| 7,658,712 B2 | 2/2010 | Klaassen et al. |
| 7,665,893 B2 | 2/2010 | Buchalter |
| 7,798,986 B2 | 9/2010 | Melvin et al. |
| 7,810,500 B2 | 10/2010 | Osterberg |
| 7,815,594 B2 | 10/2010 | Dougherty, Jr. et al. |
| 7,896,806 B2 | 3/2011 | Shah et al. |
| 7,918,004 B2 | 4/2011 | Melvin et al. |

(56) References Cited

U.S. PATENT DOCUMENTS

| | | |
|---|---|---|
| 8,062,245 B2 | 11/2011 | Gann et al. |
| 8,075,512 B2 | 12/2011 | Sargent, Jr. et al. |
| 8,083,673 B2 | 12/2011 | Rosen |
| 8,142,352 B2 | 3/2012 | Vivenzio et al. |
| 8,162,872 B2 | 4/2012 | Loyd et al. |
| 8,256,423 B2 | 9/2012 | Osterberg |
| 8,267,860 B2 | 9/2012 | Klaassen et al. |
| D671,642 S | 11/2012 | Grisby |
| 8,435,205 B2 | 5/2013 | Arora et al. |
| 8,449,491 B2 | 5/2013 | Hasse et al. |
| 8,449,492 B2 | 5/2013 | Sargent, Jr. et al. |
| 8,460,187 B2 | 6/2013 | Bouquet |
| 8,485,196 B2 | 7/2013 | Osterberg |
| 8,539,660 B2 | 9/2013 | Melvin et al. |
| 8,652,035 B2 | 2/2014 | Steigerwald |
| 8,734,414 B2 | 5/2014 | Winkel et al. |
| 8,747,308 B2 | 6/2014 | Muzzammel |
| D710,500 S | 8/2014 | Roeloffs |
| 8,834,362 B2 | 9/2014 | Shipp |
| 8,876,711 B2 | 11/2014 | Lin et al. |
| 8,926,547 B2 | 1/2015 | Arora et al. |
| 8,979,751 B2 | 3/2015 | George |
| 8,979,851 B2 | 3/2015 | Fallin et al. |
| 9,132,043 B2 | 9/2015 | Winkel et al. |
| 9,186,282 B2 | 11/2015 | Ito et al. |
| 9,233,029 B2 | 1/2016 | Gann et al. |
| 9,283,122 B2 | 3/2016 | Taniguchi et al. |
| 9,326,671 B2 | 5/2016 | Roeloffs |
| 2001/0056223 A1* | 12/2001 | Thompson ............ A61B 17/42 600/135 |
| 2002/0115910 A1 | 8/2002 | Diokno et al. |
| 2003/0069477 A1 | 4/2003 | Raisman et al. |
| 2003/0105387 A1 | 6/2003 | Frumovitz et al. |
| 2005/0021069 A1 | 1/2005 | Feuer et al. |
| 2005/0021080 A1 | 1/2005 | Feuer et al. |
| 2005/0124860 A1 | 6/2005 | Mohajer |
| 2005/0192482 A1 | 9/2005 | Carpenter et al. |
| 2005/0197615 A1 | 9/2005 | Gann et al. |
| 2005/0273044 A1 | 12/2005 | Gann et al. |
| 2005/0277867 A1 | 12/2005 | Minoguchi et al. |
| 2006/0047285 A1 | 3/2006 | Fields |
| 2006/0079924 A1 | 4/2006 | Sanders et al. |
| 2006/0084843 A1 | 4/2006 | Sommerich et al. |
| 2006/0122463 A1* | 6/2006 | Klaassen ............... A61B 1/32 600/221 |
| 2007/0032758 A1 | 2/2007 | Chase et al. |
| 2007/0032814 A1 | 2/2007 | Hibler |
| 2008/0036345 A1 | 2/2008 | Kropf et al. |
| 2008/0058605 A1 | 3/2008 | Sorensen |
| 2008/0114210 A1 | 5/2008 | Shah et al. |
| 2008/0242938 A1 | 10/2008 | Larkin |
| 2008/0262407 A1 | 10/2008 | Chase et al. |
| 2008/0287744 A1 | 11/2008 | Borodulin et al. |
| 2008/0306345 A1 | 12/2008 | Balas |
| 2009/0062691 A1 | 3/2009 | Kim |
| 2009/0099422 A1 | 4/2009 | George |
| 2011/0009803 A1 | 1/2011 | Dougherty, Jr. et al. |
| 2011/0040234 A1 | 2/2011 | Chaffringeon |
| 2011/0237902 A1 | 9/2011 | Rosen |
| 2012/0220918 A1 | 8/2012 | Chaffringeon |
| 2013/0197314 A1 | 8/2013 | Eakin |
| 2014/0081281 A1* | 3/2014 | Felder ............... A61B 17/8897 606/96 |
| 2014/0109915 A1 | 4/2014 | Reddy et al. |
| 2014/0163322 A1 | 6/2014 | Mehta |
| 2015/0057502 A1 | 2/2015 | George |
| 2015/0112148 A1 | 4/2015 | Bouquet |
| 2015/0290440 A1 | 10/2015 | Redol |
| 2017/0181605 A1 | 6/2017 | Lalli et al. |
| 2017/0181607 A1 | 6/2017 | Lalli et al. |

FOREIGN PATENT DOCUMENTS

| | | |
|---|---|---|
| CN | 201996970 U | 10/2011 |
| GB | 2424585 A | 10/2006 |
| GB | 2459076 A | 10/2009 |
| WO | WO-98/11818 A1 | 3/1998 |
| WO | WO-9833431 A1 | 8/1998 |
| WO | WO-2009000078 | 12/2008 |
| WO | WO-2011024901 A1 | 3/2011 |

OTHER PUBLICATIONS

International Search Report and Written Opinion for Application No. PCT/US2016/069045, dated Jul. 4, 2017.

* cited by examiner

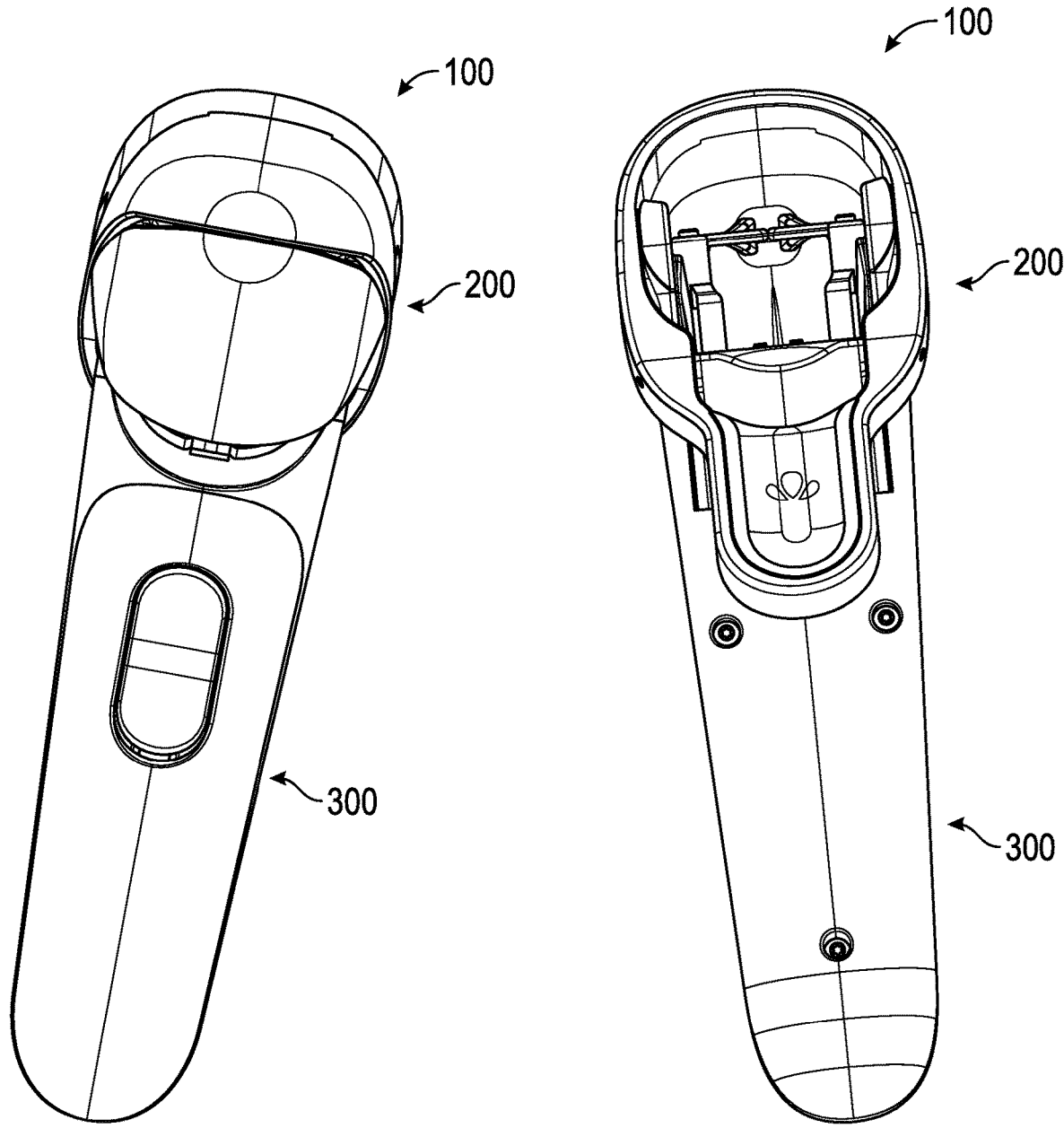
FIG.1C  FIG.1D

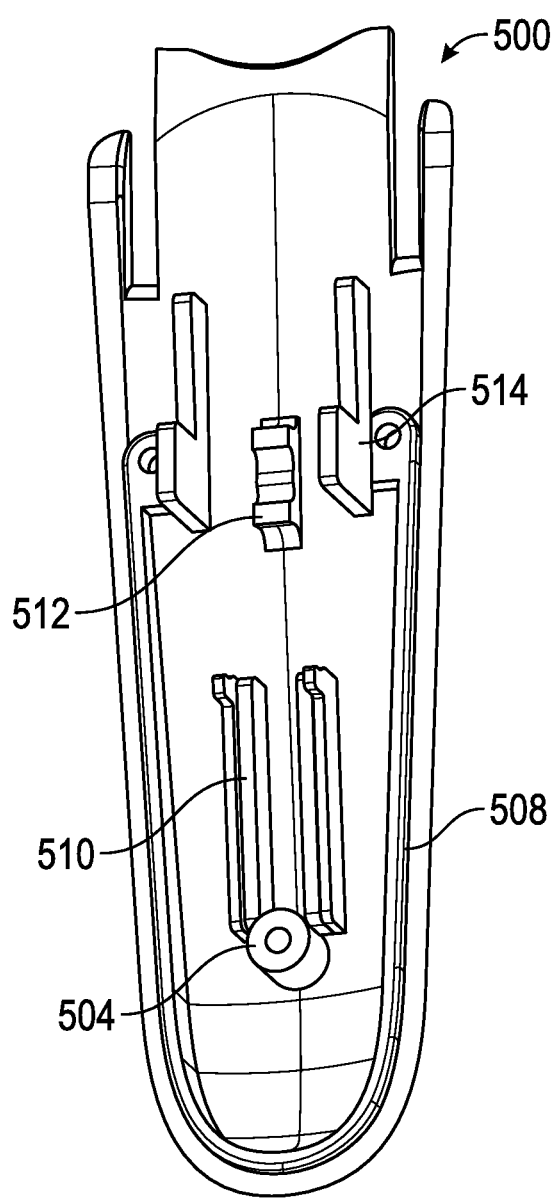 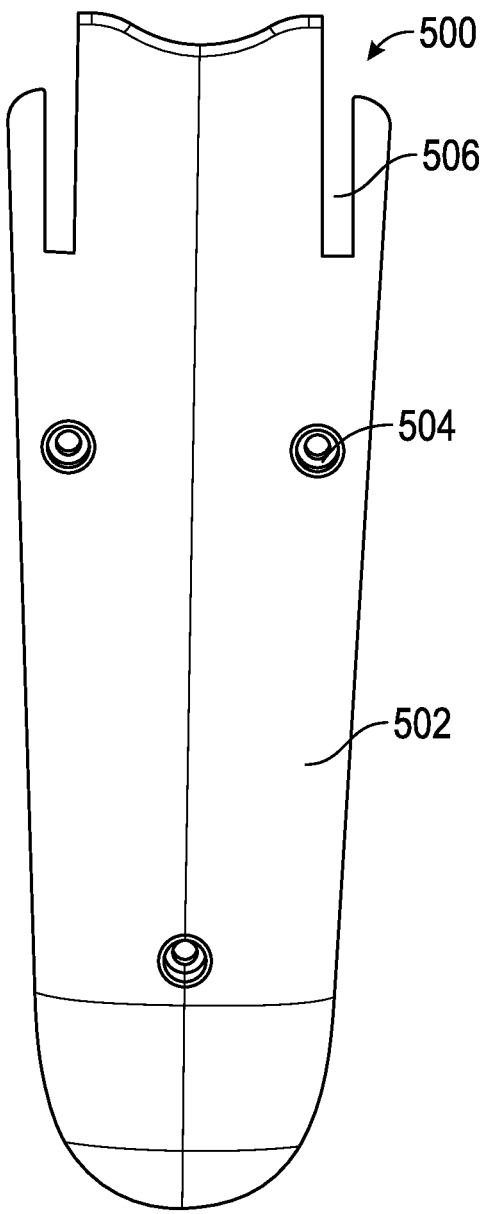
FIG. 5A  FIG. 5B

SPECULUM WITH SECONDARY BILLS

CROSS-REFERENCE TO RELATED PATENT APPLICATIONS

This application claims the benefit of and priority to U.S. Provisional Patent Application No. 62/272,625 filed Dec. 29, 2015 and entitled "Speculum Having an Expandable Body and Use Thereof," U.S. Provisional Patent Application No. 62/281,699 filed Jan. 21, 2016 and entitled "Speculum Having an Expandable Body and Use Thereof," and U.S. Provisional Patent Application No. 62/310,620 filed Mar. 18, 2016 and entitled "Speculum Having an Expandable Body and Use Thereof." This application also claims the benefit of and priority to U.S. Provisional Patent Application No. 62/272,613 filed Dec. 29, 2015 and entitled "Secondary Bills for Speculum and Use Thereof," U.S. Provisional Patent Application No. 62/281,685 filed Jan. 21, 2016 and entitled "Secondary Bills for Speculum and Use Thereof," and U.S. Provisional Patent Application No. 62/310,597 filed Mar. 18, 2016 and entitled "Secondary Bills for Speculum and Use Thereof." Each of the aforementioned provisional applications is incorporated herein by reference in its entirety.

BACKGROUND

The present disclosure relates generally to the field of medical speculum.

A speculum is a medical tool used to provide visualization into a body cavity. Speculums or specula are traditionally used for viewing and accessing the vaginal cavity for gynecology patients. The traditional vaginal speculum consists of two blades with a hinge and a handle. The blades are inserted into the body cavity in a closed position, and separated by squeezing two pieces of the handle together, thereby dilating the vagina and providing visualization of and accessibility to the vagina, the cervix, and surrounding areas. Once opened, the speculum can be locked in an open position using a screw based mechanism so an operator (e.g., physician, nurse, mid-wife, etc.) does not need to continue squeezing the pieces of the handle during the inspection. The operator can then proceed with inspecting the vagina, conducting a Pap smear or any other medical procedures that may need to be provided.

Embodiments herein generally related to improved speculum devices, components of the same, and methods of making and using the same. The devices and components overcome many drawbacks of existing speculum devices. For example, described herein according to some embodiments are speculum devices that minimize the discomfort for the patient, while providing improved accessibility and visibility for the practitioner, and minimizing repetitive stress injuries that may occur over time to practitioners.

SUMMARY OF THE INVENTION

The double blade design of the speculum devices has been in use since the 1800s and not many changes have been made to the original design. With the traditional two blade design, tissue can enter between the blades once they are opened inside the cavity, a common occurrence that providers characterize as "side wall encroachment." This can cause problems for the operators, particularly in providing clear visualization of the vagina and cervix. Women, especially obese women, women who have had multiple vaginal births, or those with vaginal laxity, have tissue in the side walls of the vagina that may fall into the space between the two blades, thereby impeding the visibility and accessibility between the blades and potentially limiting the effectiveness of the procedure. Furthermore, this may be problematic, not only with these patients, but with all patients, when trying to close the speculum, as the tissue and/or pubic hair may become pinched between the blades. Pinching of the tissue is painful for the patients and difficult for the operator to avoid without removing the speculum in an open position, which causes significant discomfort to the patient as well. There are no satisfactory solutions for these problems, resulting in tremendous patient discomfort with the entire experience.

In an attempt to limit sidewall encroachment and allow better visualization of the vaginal walls and cervix, operators may attempt to place condoms or portions of medical gloves over the speculum. This is an unsatisfactory and ineffective approach as condoms and gloves were not designed to support the internal pressure of the vaginal walls, but to be as thin as possible. Furthermore, using these solutions can result in both condoms and glove fingers, or torn portions thereof, being left behind in the vaginal cavity following removal of the speculum. Alternatively, operators may choose to use larger speculums to provide a larger viewing/accessing window even when tissue enters the sides of the speculum between the blades. However, increasing the size of the speculum can also provide discomfort to patients. While there are now different sizes of speculum offered for an examination, it can be hard to determine the correct size for a patient as the size of the patient does not necessarily correlate with the size of the speculum that should be used.

In the traditional design, speculums include a handle portion and a body portion positioned at substantially 90 degrees relative to one another. In this configuration, insertion into the vagina and maintenance in that position may be difficult and uncomfortable for the practitioner and the patient.

Furthermore, traditional designs incorporate two handle portions to be squeezed together, or a lever to be depressed, to expand the body portion of the speculum. This, too, is difficult for the practitioner with time, due to the ergonomic issues of repeated action, often multiple times a day. And finally, to hold the speculum in the opened position, speculums of the traditional metal design incorporate a screw and locking nut apparatus wherein once the desired expansion is achieved, the practitioner locks it in by screwing the nut along the shaft until it locks the speculum in place. This is problematic because it requires the practitioner to use both hands to lock in the opened position.

Speculums are traditionally made of metal, though some made with disposable plastic have been increasing in use. When the speculum is made of metal, it can feel cold upon entry, especially in comparison to the internal temperatures of the body, providing discomfort for the patient during the procedure, resulting in the patient tensing up and making the procedure more painful. However, even when made of plastic, the design of the speculum is generally the same, but for some differences that may exist in the locking mechanism, wall thickness, and consistencies between the types of plastic.

As noted above, embodiments herein generally relate to improved speculum devices, components of the same, and methods of making and using the same. The device and components overcome many drawbacks of existing speculum devices. For example, described herein according to some embodiments are speculum devices that minimize discomfort for the patient, while providing improved visibility and accessibility for the practitioner, and minimize the repetitive stress injuries that routinely occur over time. In one aspect, a set of secondary bills is provided in the speculum.

One embodiment of the invention relates to a speculum. The speculum includes a handle, a first bill and a second bill. A proximal end portion of the first bill and a proximal end portion of the second bill are coupled to an upper portion of the handle. The speculum further includes an actuation mechanism that causes both the first bill and the second bill to move simultaneously along a first axis between an open position and a closed position. In some embodiments, movement of the first bill and the second bill is symmetrical relative to the closed position.

In some embodiments, the speculum further includes a third bill and a fourth bill, wherein a proximal end portion of the third bill and a proximal end portion of the fourth bill are coupled to the upper portion of the handle and configured to open along a second axis substantially orthogonal to the first axis. In some embodiments, the actuation mechanism further causes the third bill and the fourth bill to move between an open position and a closed position. In some embodiments, the third bill and the fourth bill open simultaneously with the first bill and the second bill. In another embodiment, the third bill and the fourth bill are positioned inside of the first bill and the second bill when the first bill and the second bill are in the closed position. In some embodiments, the speculum further includes a slide coupled to the upper portion of the handle, the third bill and the fourth bill and configured to cause outward rotation of the third bill and the fourth bill to open the third bill and the fourth bill. In another embodiment, the proximal end of the first bill further includes a window frame defining a viewing window. In some embodiments, the speculum includes a thumb tab coupled to the window frame and whereby a force in a first direction on the thumb tab causes the first bill and the second bill to move between an open position and a closed position.

In some embodiments, the speculum includes a locking mechanism configured to lock the speculum in an open position. The locking mechanism includes a rocker mechanism coupled to the handle, a lock strip contained in the handle and coupled to at least one of the upper bill and the lower bill, and a pawl coupled to the handle and configured to interact with the lock strip at a first portion of the pawl and with the rocker mechanism at a second portion of the pawl. In some embodiments, the speculum is locked and unlocked by a force applied to the rocker. When the rocker is in a first position, the pawl engages with the lock strip and the speculum is locked in an open position, and wherein when the rocker is in a second position, the pawl is disengaged with the lock strip and the speculum is free to open and close without resistance. In some embodiments, the lock strip includes divots that are configured to engage with the first portion of the pawl and which prevent movement of the lock strip relative to the pawl in at least one direction when the first portion of the pawl is engaged with the divots, thereby locking the speculum in an open position.

In some embodiments, the speculum further includes an angle between the handle and at least one of the first and the second bill, when the first and the second bill are in the closed position, and wherein the angle is in the range of 100 degrees to 180 degrees. In some embodiments, all edges and shape transitions on an outer surface of the handle are rounded. In some embodiments, the speculum further includes a gripping portion. In some embodiments, the gripping portion includes at least a portion made of a different material than a material of the speculum. In some embodiments, the gripping portion comprises an overmold placed over the handle. In some embodiments, the speculum includes a lighting module and/or a camera system. In some embodiments, the speculum has a narrower width than traditional speculum.

Another embodiment relates to a locking mechanism for a speculum. The locking mechanism includes a rocker mechanism coupled to the speculum, a lock strip contained in a handle of the speculum and coupled to at least one of an upper bill and a lower bill of the speculum, and a pawl coupled to the handle and configured to interact with the lock strip at a first portion of the pawl and with the rocker mechanism at a second portion of the pawl.

In some embodiments, the speculum is locked and unlocked by a force applied to the rocker. When the rocker is in a first position, the pawl engages with the lock strip and the speculum is locked in an open position, and when the rocker is in a second position, the pawl is disengaged with the lock strip and the speculum is free to open and close without resistance. In some embodiments, the lock strip comprises divots that are configured to engage with the first portion of the pawl and which prevent movement of the lock strip relative to the pawl in at least one direction when the first portion of the pawl is engaged with the divots, thereby locking the speculum in an open position.

Yet another embodiment relates to a method of using a speculum. The method includes inserting a speculum into a vaginal cavity of a female patient and simultaneously actuating a first bill and a second bill of the speculum to cause both the first bill and the second bill to move between an open position and a closed position to dilate the vaginal cavity.

In some embodiments, the method further includes actuating a third bill and a fourth bill to cause separation of the third bill and a fourth bill in a directional orthogonal to the separation of the first bill and the second bill. In some embodiments, actuating the first bill and the second bill occurs simultaneously with actuating the third bill and the fourth bill.

BRIEF DESCRIPTION OF THE DRAWINGS

FIG. 1C is a front view of the speculum of FIG. 1A.

FIG. 1D is a rear view of the speculum of FIG. 1A.

FIG. 5A is a back perspective view of a handle cover of the speculum of FIG. 1A.

FIG. 5B is a front perspective view of the handle cover of FIG. 5A.

DETAILED DESCRIPTION

Figure 1A:
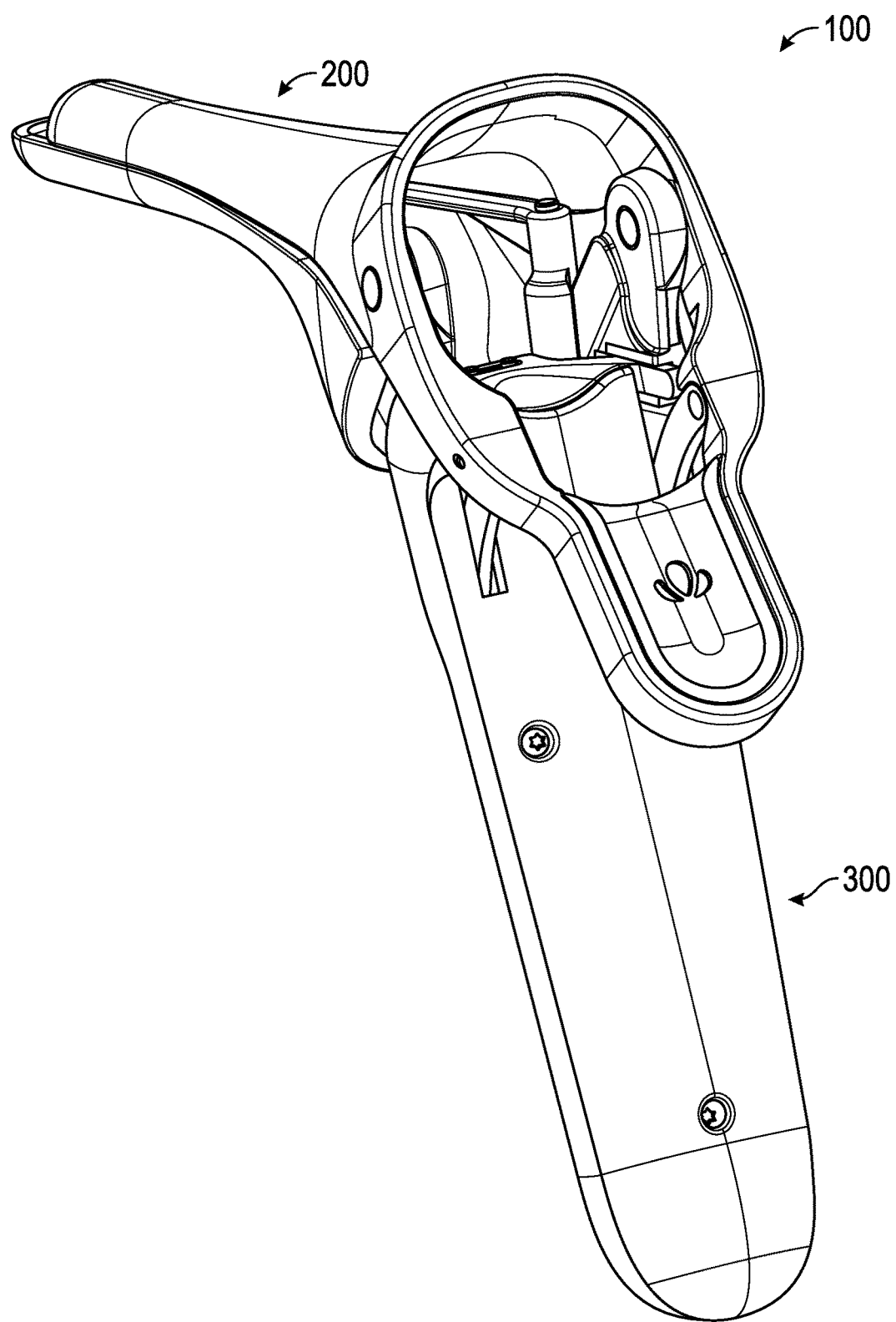
FIG. 1A is a side view of a speculum in accordance with one embodiment, shown in an insertion position.
Figure 1B:
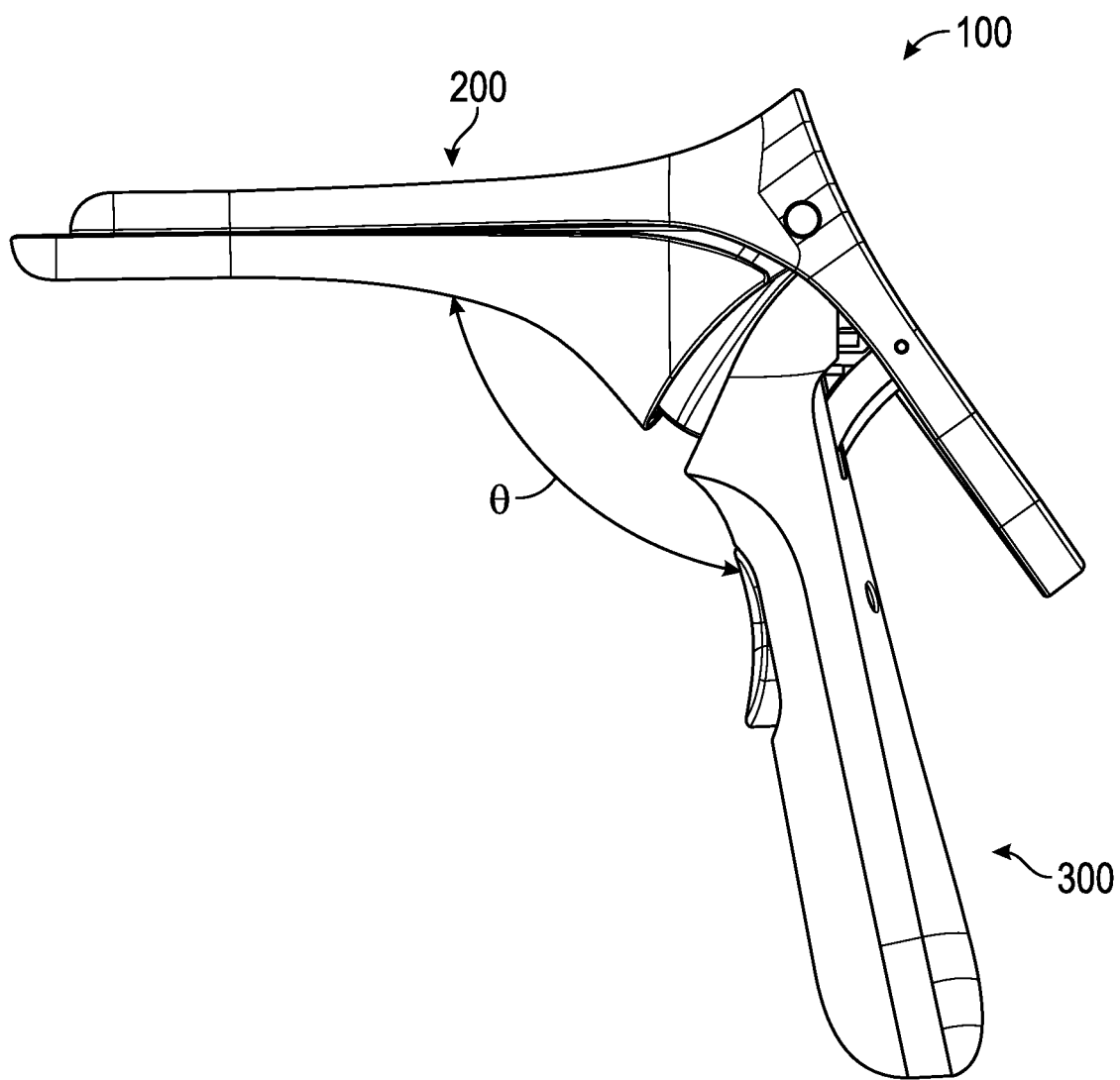
FIG. 1B is a rear perspective view of the speculum of FIG. 1A.

In the following detailed description, reference is made to the accompanying drawings, which form a part of the present disclosure. In the drawings, similar symbols typically identify similar components, unless context dictates otherwise. The illustrative embodiments described in the detailed description, drawings, and claims are not meant to be limiting. The detailed description is intended as a description of exemplary embodiments and is not intended to represent the only embodiments which may be practiced. The term "exemplary," as used herein, means "serving as an example, instance, or illustration," and should not necessarily be construed as preferred or advantageous over other embodiments. Other embodiments may be utilized, and other changes may be made, without departing from the spirit or scope of the subject matter presented here. It will be readily understood that the aspects of the present disclosure, as generally described herein, and illustrated in the Figures, can be arranged, substituted, combined, and designed in a wide variety of different configurations, all of which are explicitly contemplated and form part of this disclosure.

Referring to the Figures generally, a speculum is shown. The speculum has an updated design relative to the antiquated, traditional two-bill design. In some embodiments, the speculum has two additional bills that are integrated with a speculum having two bills. The profile of the speculum may be narrower than traditional speculum, making it more comfortable for patients, because the secondary bills reduces some of the previously described shortcomings of the traditional design, for example, the problem of side wall tissue falling into the user's line of sight. In particular, while traditional speculum typically employ bills having a width between 20 mm and 40 mm, the bills of the present speculum may have a width between approximately 12 mm and 20 mm. The speculum also has an ergonomic handle design for increased comfort during use by the clinician.

Referring now to FIGS. 1A-1E, a speculum 100 is shown in accordance with one embodiment. The speculum 100 includes a bill portion 200 and a handle portion 300. The speculum may be made of any sturdy biomaterial including metals and plastics. The bill portion 200 is coupled to the handle portion 300 and the bill portion is movable between an open position and a closed position. The bill portion 200 may be configured in such a way that when in the closed position, the bill portion may be wide near the handle portion 300, creating a cone shape as the bill portion 200 extends away from the handle portion 300. The bill portion 200 may maintain a constant shape after the cone, creating an elongated shape.

When the bill portion 200 is in a closed position, as seen in FIGS. 1A-1D, the speculum 100 can be inserted in a patient's vagina. The bill portion 200 is placed in line with an opening of the vagina and applied a force parallel to the bill portion 200 to push the bill portion 200 into the vagina. The user may position the speculum 100 at a depth of the vagina to provide a clear view of the cervix when the bill portion 200 is opened. The speculum 100 may be inserted in a vertical direction, as seen in FIGS. 1A-1D. Alternatively, the speculum 100 may be inserted in a horizontal direction and rotated to a vertical position once inside the vagina. The speculum 100 may be inserted into the vagina at a 45 degree angle to increase the comfort of the user. The speculum may be inserted so that an end of the bill portion 200 are located below the cervix. Once the bill portion 200 is opened, as seen in FIG. 1E, the cervix may then fall into the viewing opening created by the separation of the bill portion 200. Alternatively, the speculum 100 may be moved around once inserted into the vagina to provide a clear view and adequate accessibility of the cervix.

The speculum 100 may also be equipped with a camera system. The camera system may provide images, video, or a combination thereof. The speculum 100 may additionally be equipped with a system capable of transmitting images and/or video to a monitor, allowing the patient and/or user to simultaneously visualize the procedure. The transmission of images and/or video may occur wirelessly via Bluetooth, Wi-Fi, or other suitable technology.

In some embodiments, the distal portion of the bill portion 200 may optionally be coated with one or more therapeutic/bioactive agents or lubricants. Examples of suitable bioactive agents include, but are not limited to, hormonal and non-hormonal contraceptive agents, cancer screening agents, vaginal spermicides, vaginal microbicides, antibacterial agents, antifungal agents, antiviral agents, anti-HIV agents and cancer treatment agents, or combinations thereof. The therapeutic agents may be in any suitable formulation that may be applied to the surface of a vaginal speculum, such as liquid, gel and powder.

FIGS. 1A-1D may include an updated ergonomic handle in accordance with certain embodiments of the speculum 100. The ergonomic handle employs a greater angle θ between the bill portion 200 and the handle portion 300, which is more comfortable for both the practitioner and the patient during use. The handle portion 300 may also have a textured grip, for example, including bumps, dimples, and/or other texturizing elements, and a rounded or formed body for comfort and ergonomic benefit.

The handle portion 300 is positioned so as to create an angle θ between the bill portion 200 and the handle portion 300. In some embodiments, the angle θ is be greater than 90 degrees but less than 180 degrees. In other embodiments, the angle θ is between 100 degrees and 180 degrees. In some embodiments the angle θ is about 95, 100, 105, 110, 115, 120, 125, 125, 130, 135, 140, 145, 150, 155, 160, 165, 170 or 180 degrees. The angle θ provides a more comfortable angle for the user to insert the speculum 100 into the vagina of the patient. In addition, the angle θ provides more room for the hand of the user when inserting the speculum 100. This reduces the risk of the hand of the user coming in contact with the patient when inserting the speculum 100, which can be uncomfortable and awkward for the patient. The angle θ also provides a more comfortable angle for a wrist of the user during the procedure. This reduces the risk of injury or strain to the hand or wrist of the user, especially when the user completes multiple procedures in a single day, or day after day.

FIG. 1E shows the speculum 100 in an open position. When in the open position, the bill portion 200 of the speculum 100 is expanded, by moving both an upper bill 600 and a lower bill 700 away from the closed position. As shown, the upper bill 600 and the lower bill 700 move symmetrically away from the closed position. In certain exemplary embodiments, opening the upper bill 600 and lower bill 700 also reveals and separates a right secondary bill 900 and a left secondary bill 950. In the open position, the upper bill 600 and the lower bill 700 separate the tissue of the vagina, while the right and left secondary bills 900 and 950 aid in retaining side wall tissue of the vagina to maintain a clear viewing window for the user.

The handle portion 300 may include a grip 110. The grip 110 may be of a material that provides more traction for the hand of the user. In some embodiments, the grip 110 is textured to provide more traction for the hand of the user. The grip 110 may allow the user to apply less force with the hand of the user in order to hold the speculum 100. By allowing the user to use less force to hold the speculum, the user may become less fatigued when performing the procedure. In addition, when less force is needed, the user may experience less cramps, strains and/or injuries caused by using the speculum 100. The grip 110 may extend a length of the handle portion 300. In some embodiments, the grip 110 only extends a portion of the length of the handle portion 300. In another embodiment, the grip 110 wraps around the circumference of the handle portion 300. In yet another embodiment, the grip 110 is a plurality of pieces spaced along the handle portion 300. In another embodiment, the grip 110 is made of grooves located along the handle portion 300, where the grooves align with where fingers of the user would be located when holding the handle portion 300.

The handle 300 and/or the speculum 100 may be made of metal and/or plastic, including, but not limited to, titanium, aluminum, stainless steel, acrylic, polyethylene, polyester, polyethyleneaphthlate, polystyrene, polyvinylchloride, polyethersulfone, polyetherimide, polycarbonate, polysulfone, polyetheretherketone, polyphenylsulfone, and polymethyl methacrylate. The handle 106 may be made of a material that can be sterilized. The handle 106 may be made of material that is biocompatible. The handle 300 and/or the speculum 100 may be made using a variety of techniques including, but not limited to, injection molding, extrusion, machining, blow molding, rotational molding, compression molding, transfer molding, stamping, and casting.

Figure 1E:
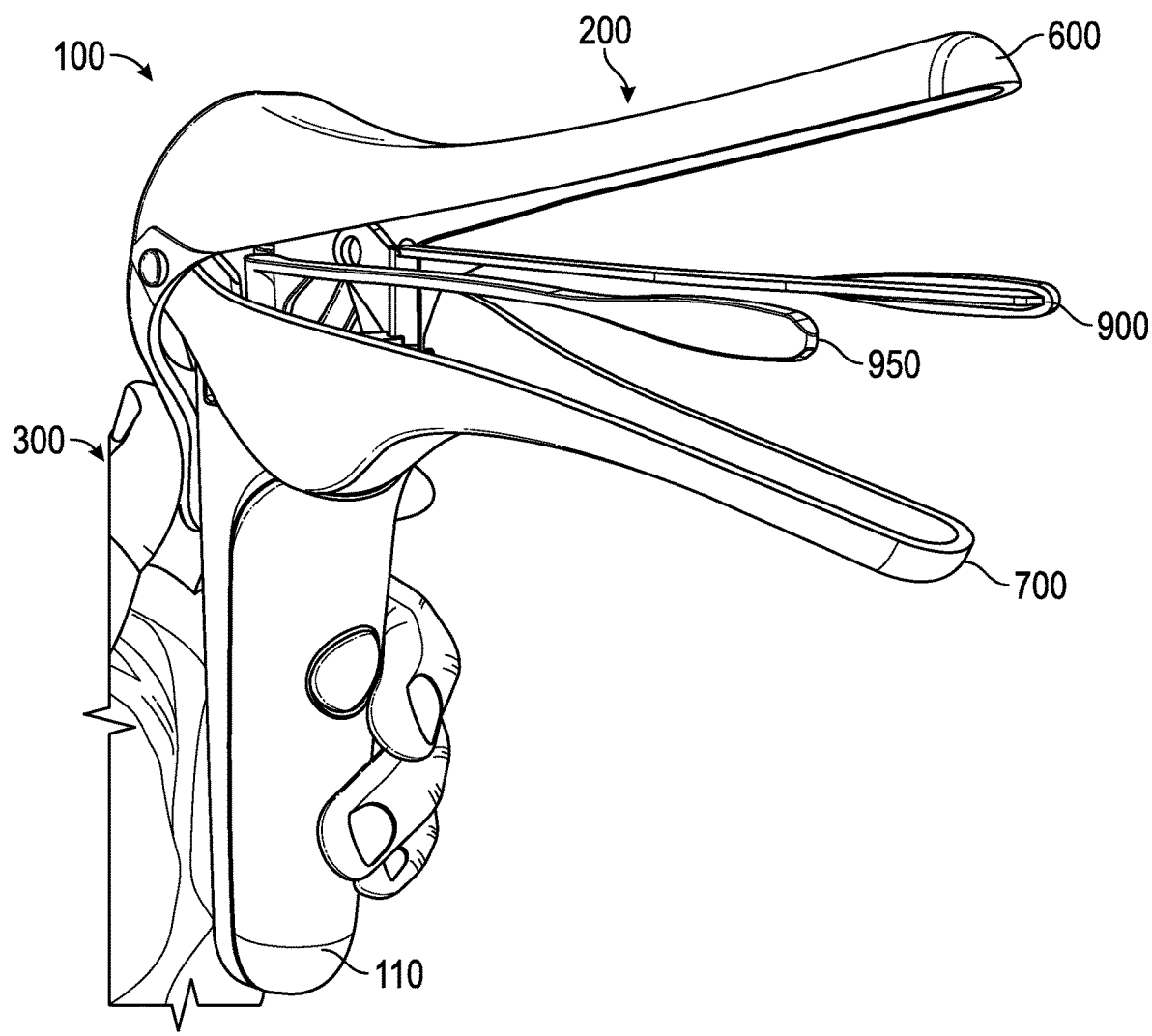
FIG. 1E is a perspective view of the speculum of FIG. 1A in an open position.
Figure 2:
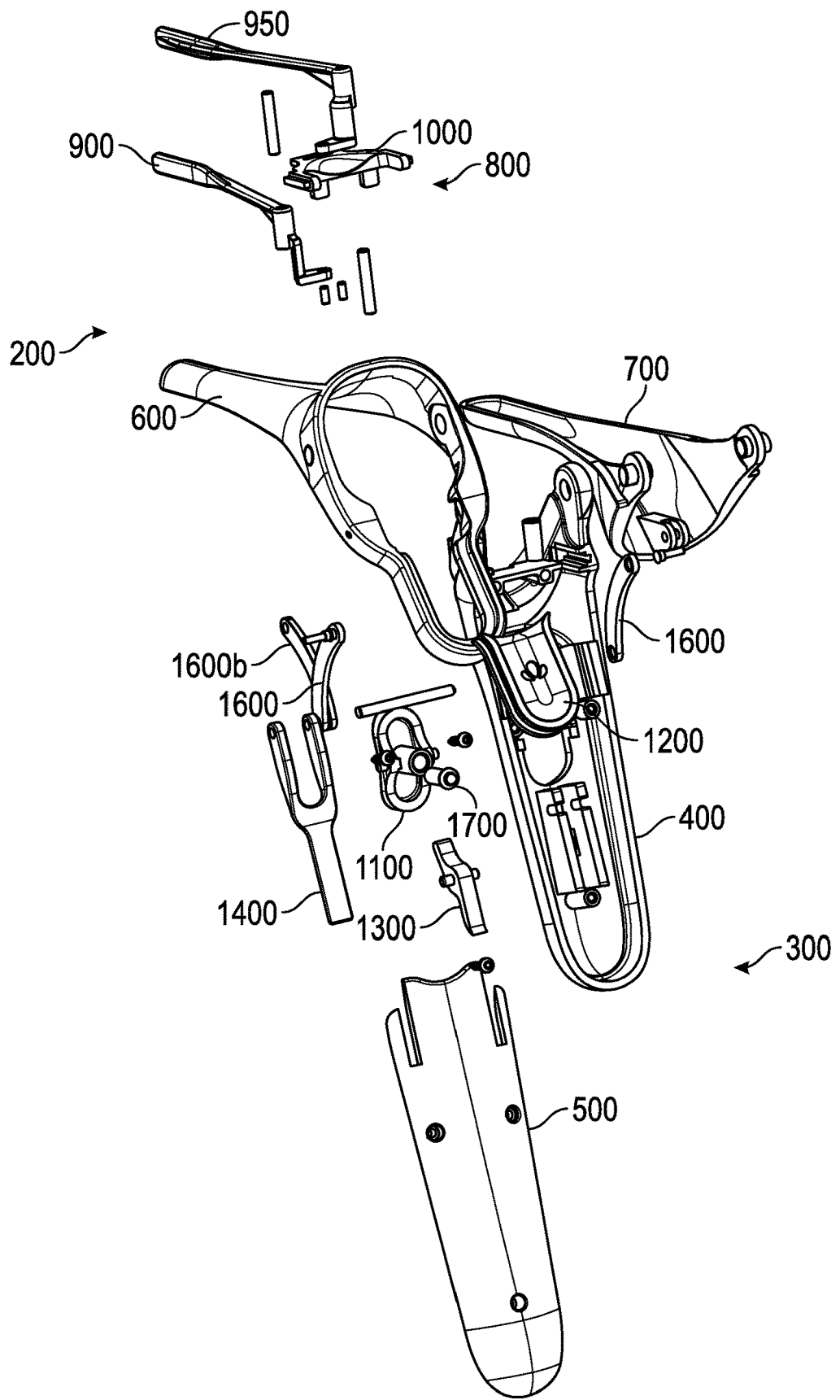
FIG. 2 is an exploded view of the speculum of FIG. 1A.
Figure 3:
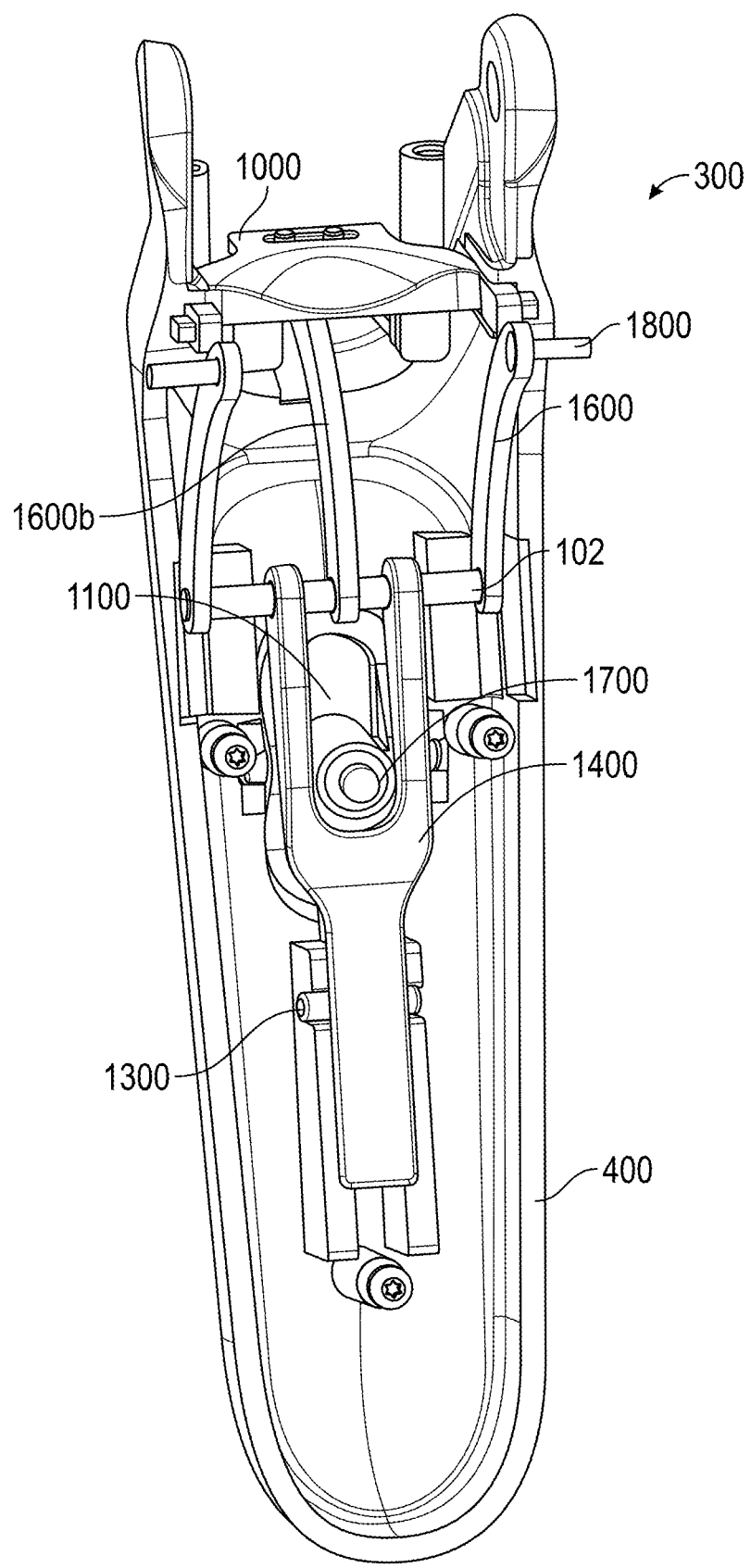
FIG. 3 is view of an interior of a handle of the speculum of FIG. 1A.

FIG. 2 is an expanded view of the speculum 100 with secondary bills of FIG. 1A showing components of the bill portion 200 and the handle portion 300. The handle portion 300 includes a handle 400, a handle cover 500, and an actuation mechanism including links 1600 and 1600b, and dowel 102, and a locking mechanism including a rocker 1100, a pawl 1300, a lock strip 1400, and a ball plunger 1700 (see also FIG. 3). The bill portion 200 includes the upper bill 600, the lower bill 700, a secondary bill assembly 800, and a thumb tab 1200. The secondary bill assembly 800 includes the right secondary bill 900, the left secondary bill 950, and a slide 1000. The actuation mechanism causes opening and closing of the upper bill 600, lower bill 700, the right secondary bill 900 and the left secondary bill 950. Each of the components will be described in detail below.

Figure 4A:
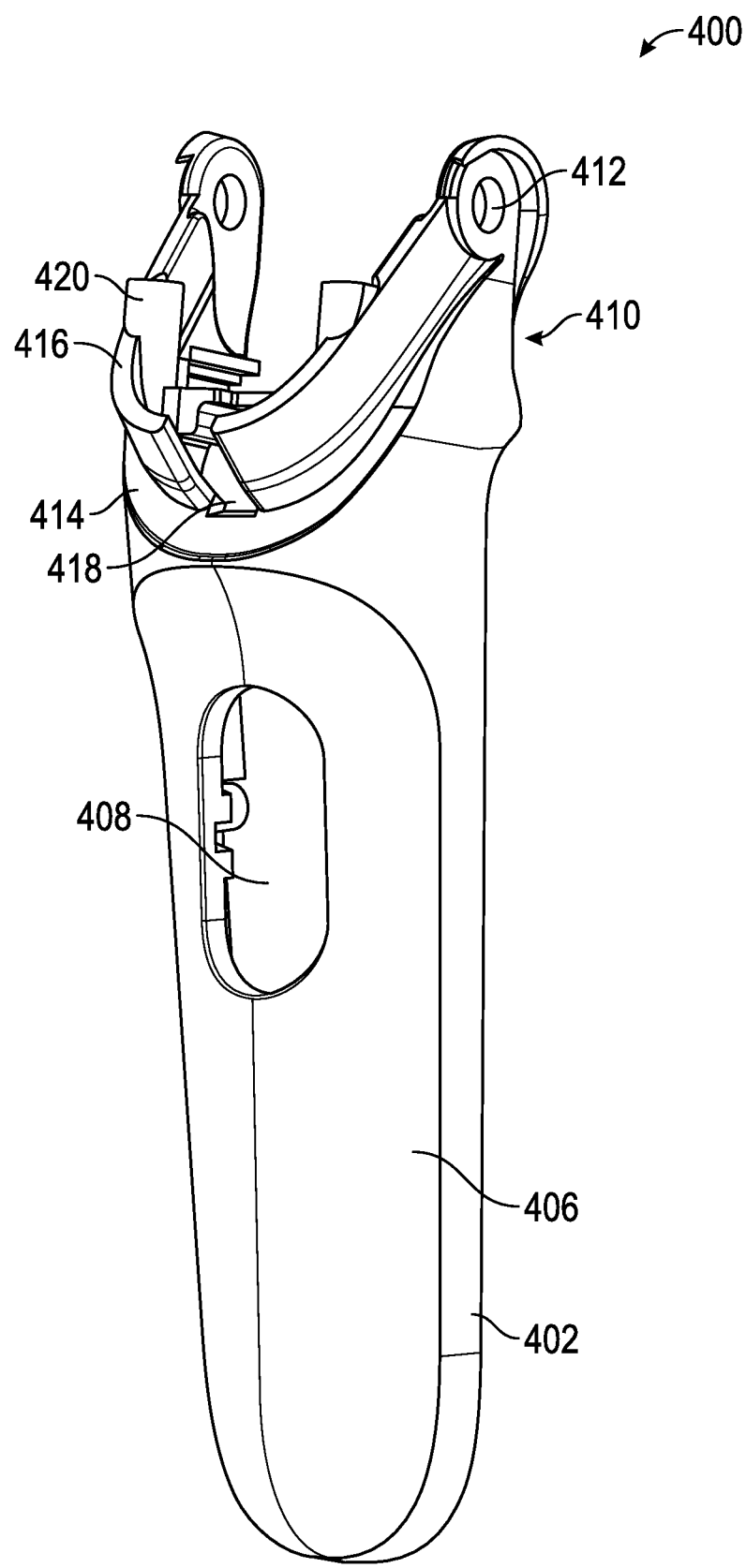
FIG. 4A is a front perspective view of the handle of the speculum of FIG. 1A.
Figure 4B:
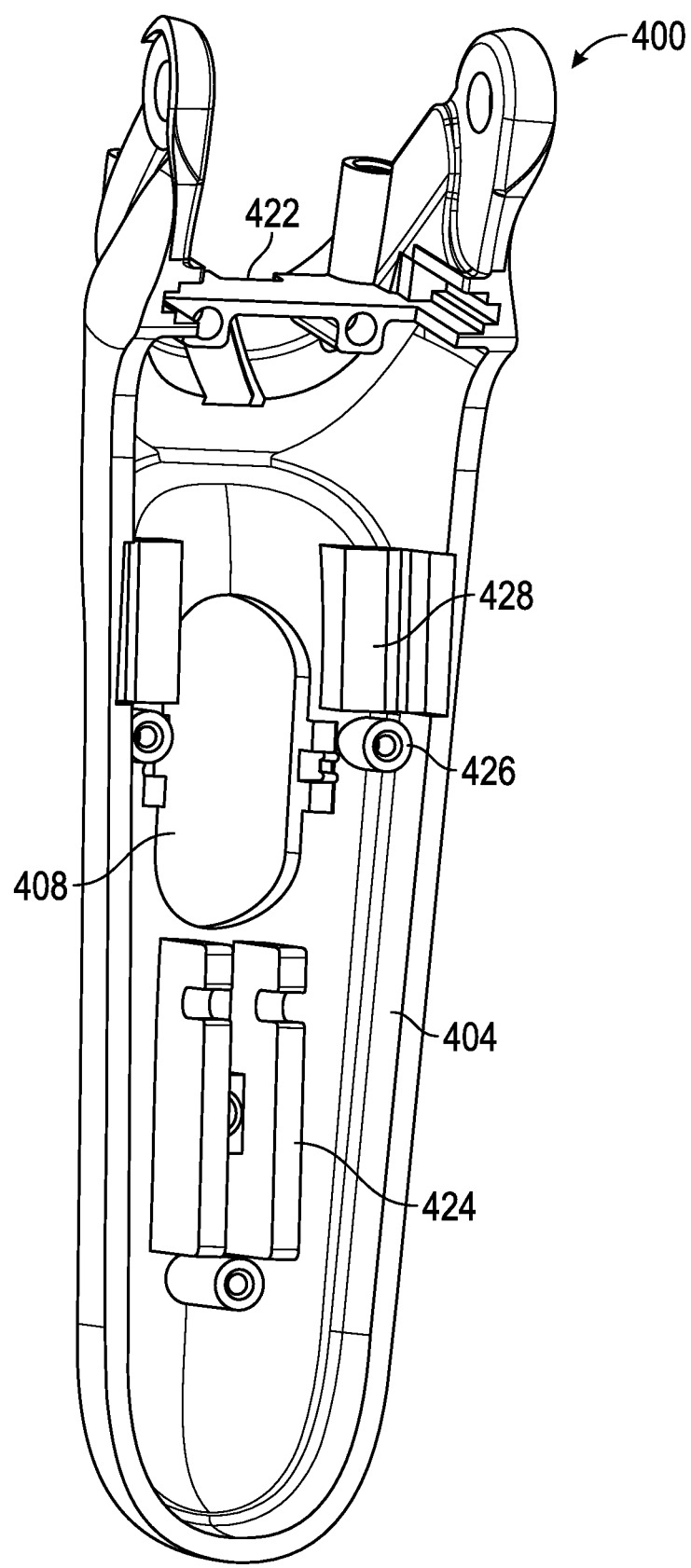
FIG. 4B is a back perspective view of the handle of FIG. 4A.

Referring to FIGS. 4A and 4B, the handle 400 of the speculum 100 with secondary bills is shown. The handle 400 includes an external cover 402 and an internal configuration 404. The external surface 402 has a rounded surface 406 that is configured to provide an ergonomic surface for a hand of a user (e.g., a nurse, practitioner, physician, etc.). The rounded surface 406 includes an aperture 408 to receive the rocker 1100. The handle 400 also includes a coupling portion 410 that is configured to couple the bill portion 200 to the handle 400. The coupling portion 410 includes apertures 412 to receive the lower bill 700. The coupling portion 410 also includes a ridge 414 and a wall 416 that support the lower bill 700. The wall 416 includes a slot 418 for a link 1600b to extend through to allow actuation of the lower bill 700. The coupling portion 410 also includes cylindrical supports 420 that couple the left and right secondary bills 900 and 950 to the handle 400.

The internal configuration 404 includes a slide coupler 422 that receives the slide 1000. The internal configuration 404 also includes extensions 424 that house the pawl 1300 and provides a stop for the lock strip 1400. The internal configuration 404 also includes screw holes 426 that provide coupling between the handle 400 and the handle cover 500. The internal configuration 404 also includes ledges 428 that receive links 1600 to allow actuation of the bill portion 200.

Referring to FIGS. 5A and 5B, the handle cover 500 of the speculum 100 is shown. The handle cover 500 includes an external surface 502 that is configured to provide an ergonomic surface for a hand of the user. The external surface 502 also includes apertures 504 that provide coupling between the handle 400 and the handle cover 500 via screws. The handle cover 500 also includes slots 506 that provide access for links 1600 to connect the handle 400 to the upper bill 600.

The handle cover 500 also includes an interior 508. The interior 508 includes ridges 510 to support the lock strip 1400. The interior 508 also includes an indent 512 that abuts the ball plunger 1700. The interior 508 also includes guides 514 that provide guidance of the lock strip 1400.

Figure 6:
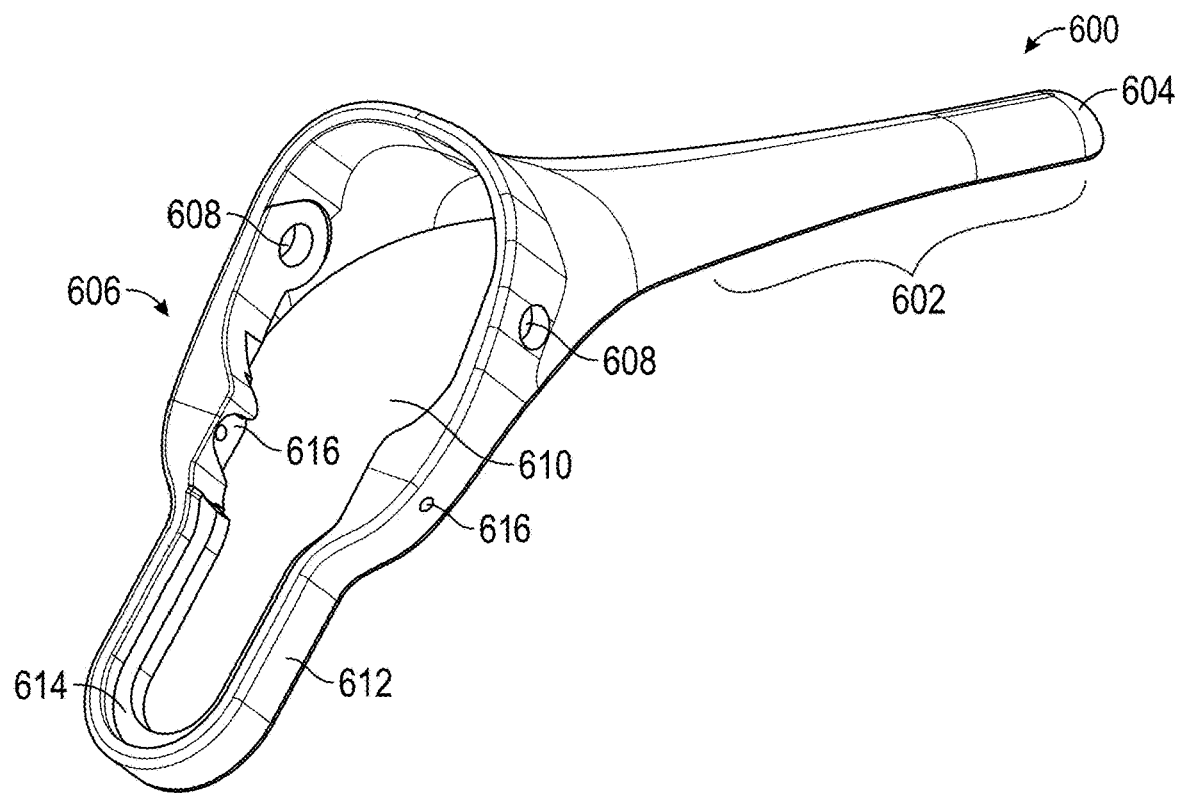
FIG. 6 is a perspective view of an upper bill of the speculum of FIG. 1A.

Referring to FIG. 6, the upper bill 600 of the speculum 100 is shown. The upper bill 600 includes an elongated portion 602. The elongated portion 602 may have a width that is larger than a height of the elongated portion 602, creating an oblong shape. Alternatively, the height and width of the elongated portion 602 may be configured in such a way that when the upper bill 600 and the lower bill 700 are closed, a circular cross section is formed. At an end 604 of the elongated portion 602, away from a handle region 606, may be rounded. The rounded end 604 may provide more comfort to a patient whom will be receiving the speculum 100 in a cavity. The upper bill 600 and the lower bill 700 may also be configured such that when in the closed position, the end 604 of the upper bill 600 is more proximal than the end 704 of the lower bill 700 (in other words, lower bill 700 extends farther than upper bill 600), thereby the creating a gap to prevent tissue from becoming lodged in between the upper bill 600 and the lower bill 700 during insertion. In other embodiments, however, the two ends 604 and 704 may abut one another, providing no gap. The upper bill 600 and the lower bill 700 may have a semi-circular cross section along a length of the upper bill 600 and the lower bill 700, where the flat portions of the semi-circles are moved together when the upper bill 600 and the lower bill 700 are in a closed position. Alternatively, an outer edge and an inner edges of the upper bill 600 and the lower bill 700 are circular, such that when the upper bill 600 and the lower bill 700 are in the closed position, a cross section of the upper bill 600 and the lower bill 700 is a ring shape. A ring shape cross section may provide a larger viewing opening for a user when the upper bill 600 and the lower bill 700 are in the open position.

The upper bill 600 also includes a window frame 606. The window frame 606 includes apertures 608 to couple the upper bill 600 to the lower bill 700 and the handle 400. The apertures 608 may be accompanied by a slight indentation. The window frame 606 is wider than the elongated portion 602 to provide a window 610 so that when the upper bill 600 and the lower bill 700 are in the open position, the user has an opening to view the vagina and cervix. The window 610 may be circular, oblong, rectangular, or any other shape that would provide an opening for viewing. The window 610 should be of sufficient size and shape to allow the user to see the entire opening created when the upper bill 600 and the lower bill 700 are in the open position. Referring back to FIG. 1A, the window frame 606 extends at an angle $\Phi$ away from handle 300. In some embodiments, the angle $\Phi$ is greater than 25 degrees but less than 40 degrees, or any degree value or sub range of degrees therein. In some embodiments, the angle may be between 30 and 35 degrees. In some embodiments the angle $\Phi$ is about 25, 26, 27, 28, 29, 30, 31, 32, 33, 34, 35, 36, 37, 38, 39, 40, 41, 42, 43, 44, or 45 degrees.

The window frame 606 also includes an actuation region 612 that receives a thumb tab 1200 (see FIG. 7) to provide actuation of the upper bill 600. The actuation region 612 also includes a ridge 614 to secure the thumb tab 1200 in the upper bill 600. The actuation region 612 is narrower than the viewing window 610 such that the thumb tab 1200 can be slid into the actuation region 1200. The window frame 606 also includes two indentations 616 that fit a link 1600 on either side. The links 1600 are coupled to the window frame 606 and the indentations 616 via the hinge pins 1800.

Figure 7:
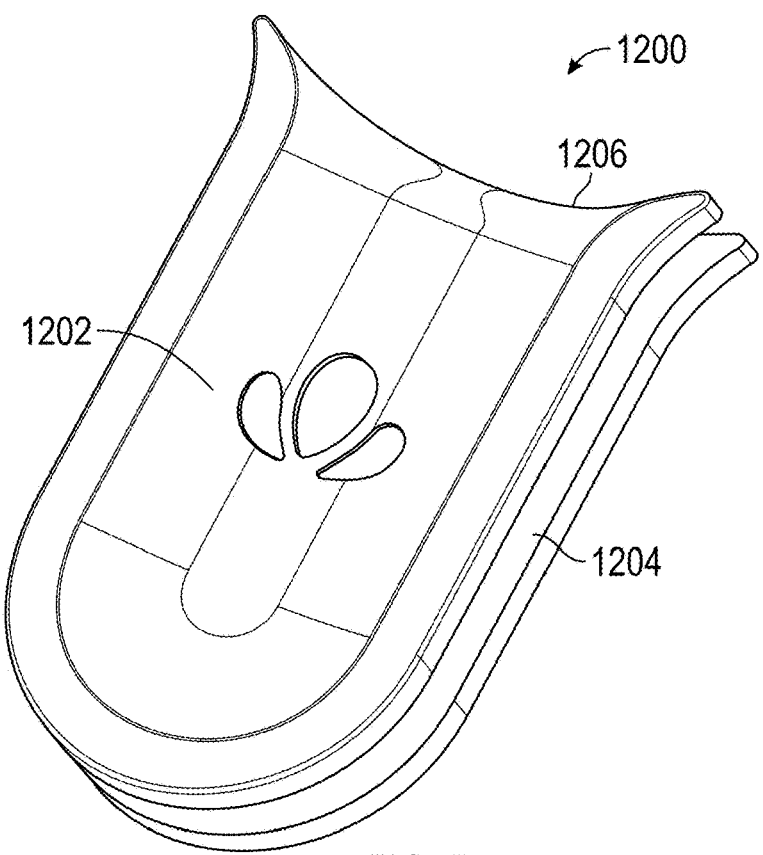
FIG. 7 is a perspective view of a thumb tab of the speculum of FIG. 1A.

Referring to FIG. 7, the thumb tab 1200 is shown. The thumb tab provides the actuation mechanism for the speculum of the exemplary embodiment shown in the figures. The thumb tab 1200 includes a top surface 1202 to provide a rigid surface for the user to apply a force. The thumb tab 1200 also includes a groove 1204 that receives the ridge 614 of the upper bill 600. A top 1206 of the thumb tab has a curvature provided to maintain an ample viewing window for the user. A force is applied by a thumb of the user to the thumb tab 1200 and causes the upper bill 600 and the lower bill 700, as well as the right and left secondary bills 900 and 950 to separate. The force applied to the thumb tab 1200 should not need to be a substantial force. In some embodiments, a distance the thumb tab 1200 moves correlates to a distance the upper bill 600 and the lower bill 700 separate. In this regard, the user would be able to select a specific distance between the upper bill 600 and the lower bill 700 for each patient. The upper bill 600 and the lower bill 700 may open in a continuous fashion when force is continuously applied to the thumb tab 1200. Alternatively, the force applied to the thumb tab 1200 may cause the upper bill 600 and the lower bill 700 to only open a specified distance (e.g., one fourth of the total distance the upper bill 600 and the lower bill 700 can separate). The user would apply force multiple times to separate the upper bill 600 and the lower bill 700 the desired distance.

When the force is applied to the thumb tab 1200, the opening created by the separation of the upper bill 600 and the lower bill 700 may be caused by both the upper bill 600 and the lower bill 700 moving, or either the upper bill 600 and the lower bill 700 moving. For example, the force applied on the thumb tab 1200 may cause the upper bill 600 to move, while lower bill 700 remains stationary.

Figure 8:
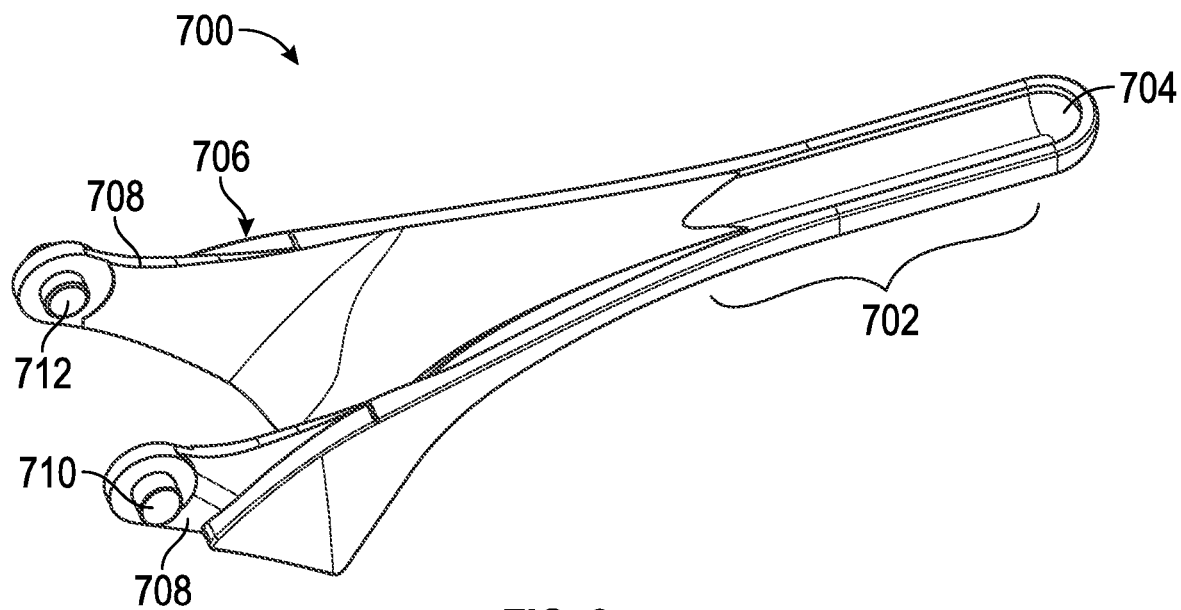
FIG. 8 is a perspective view of a lower bill of the speculum of FIG. 1A.

Referring to FIG. 8, the lower bill 700 of the speculum 100 is shown. The lower bill 700 includes an elongated portion 702. The elongated portion 702 may have a width that is larger than a height of the elongated portion 702, creating an oblong shape. Alternatively, the height and width of the elongated portion 702 may be configured in such a way that when the upper bill 600 and the lower bill 700 are closed, a circular cross section is formed. At an end 704 of the elongated portion 702, away from an actuation region 706, may be rounded. The rounded end 704 may provide more comfort to a patient whom will be receiving the speculum 100 in a cavity.

The actuation region 706 may include extensions 708. The extensions 708 are coupled to an exterior coupling knob 710 and an interior coupling knob 712. The interior coupling knob 710 couples the lower bill 700 to the handle 400. The exterior coupling knob 712 couples the lower bill 700 to the upper bill 600.

The lower bill 700 is coupled to a link 1600*b* that is caused to move in coordination with the rotation of the upper bill 600. Specifically, the link 1600*b* is coupled at a first end to the upper bill 700 and at a second end to dowel 102. As the upper bill 600 moves between a closed and an open position, dowel 102 moves via links 1600, which acts on link 1600*b* and thereby causes coordinated movement between the closed and the open position of lower bill 700. In other embodiments, however, upper bill and lower bill may be individually actuated. In some such embodiments, upper bill and lower bill do not move simultaneously between the open and the closed position.

Figure 9:
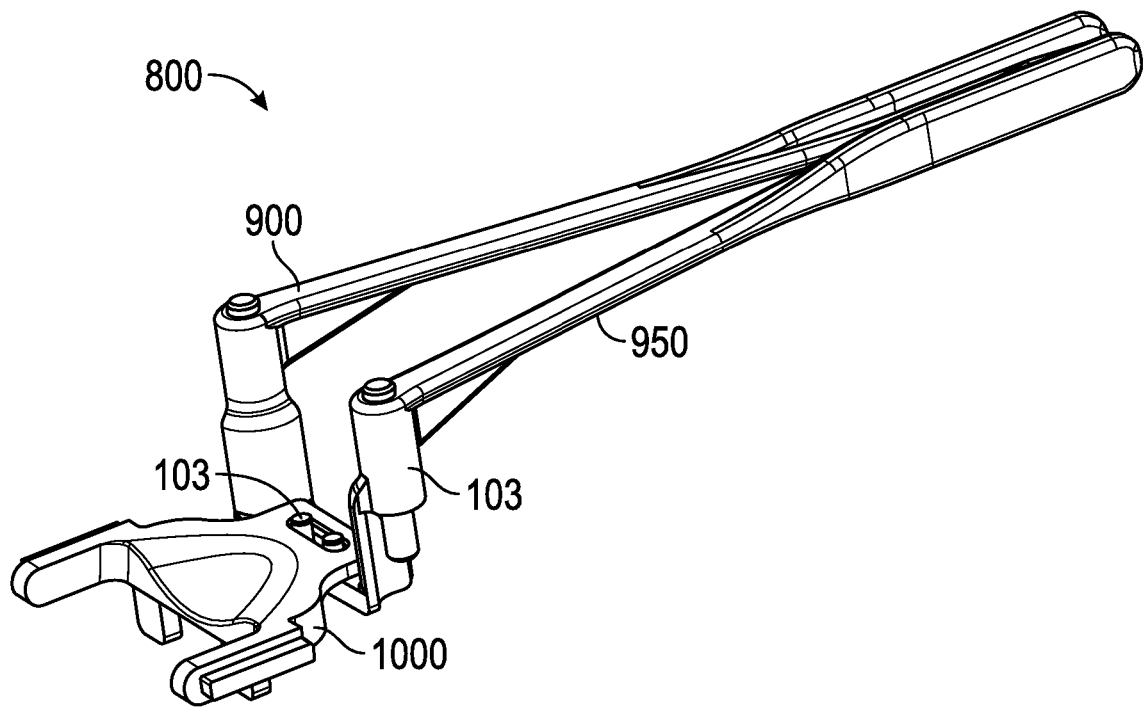
FIG. 9 is a perspective view of secondary bills assembly of the speculum of FIG. 1A.
Figure 10A:
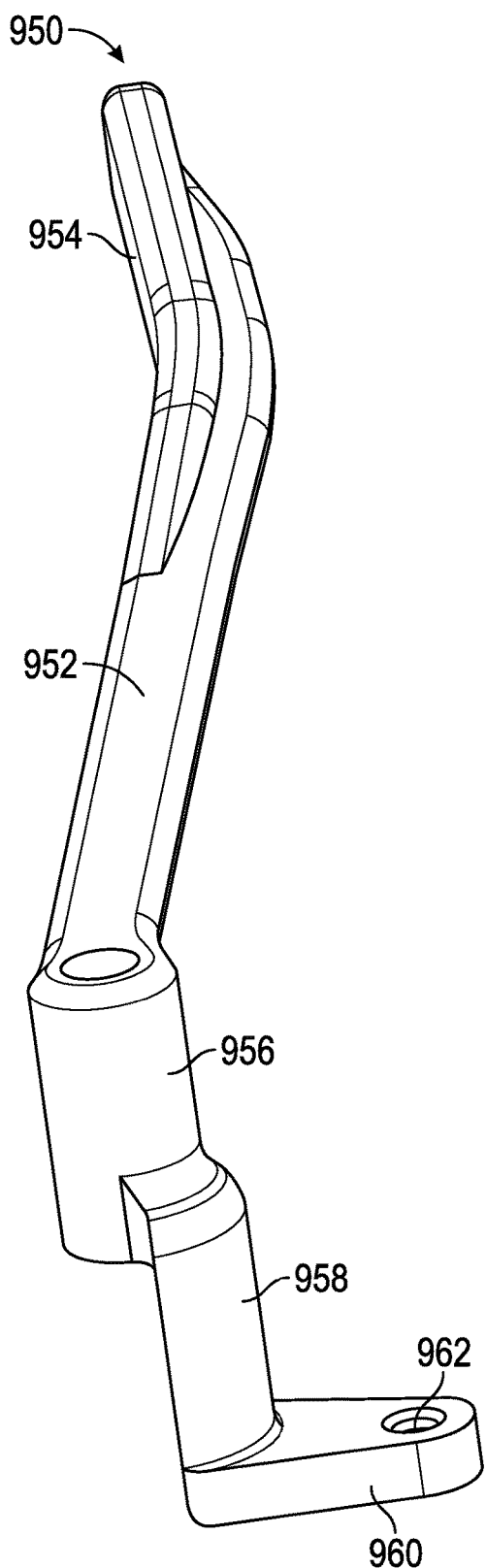
FIG. 10A is a perspective view of a right secondary bill of the speculum of FIG. 1A.
Figure 10B:
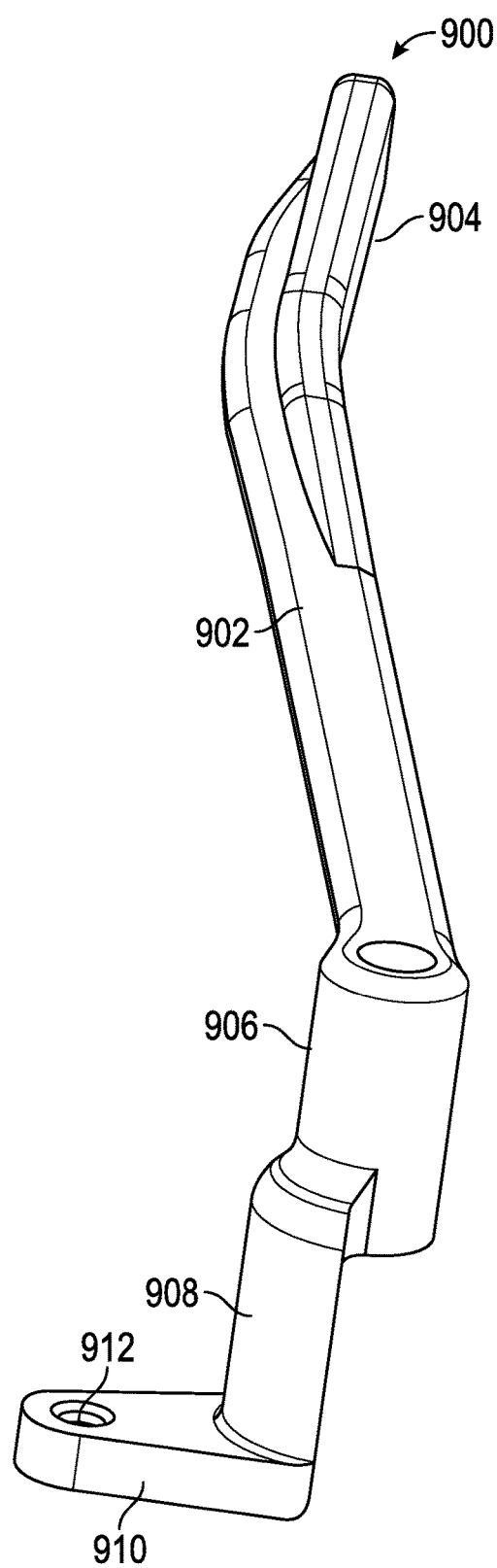
FIG. 10B is a perspective view of a left secondary bill of the speculum of FIG. 1A.
Figure 11A:
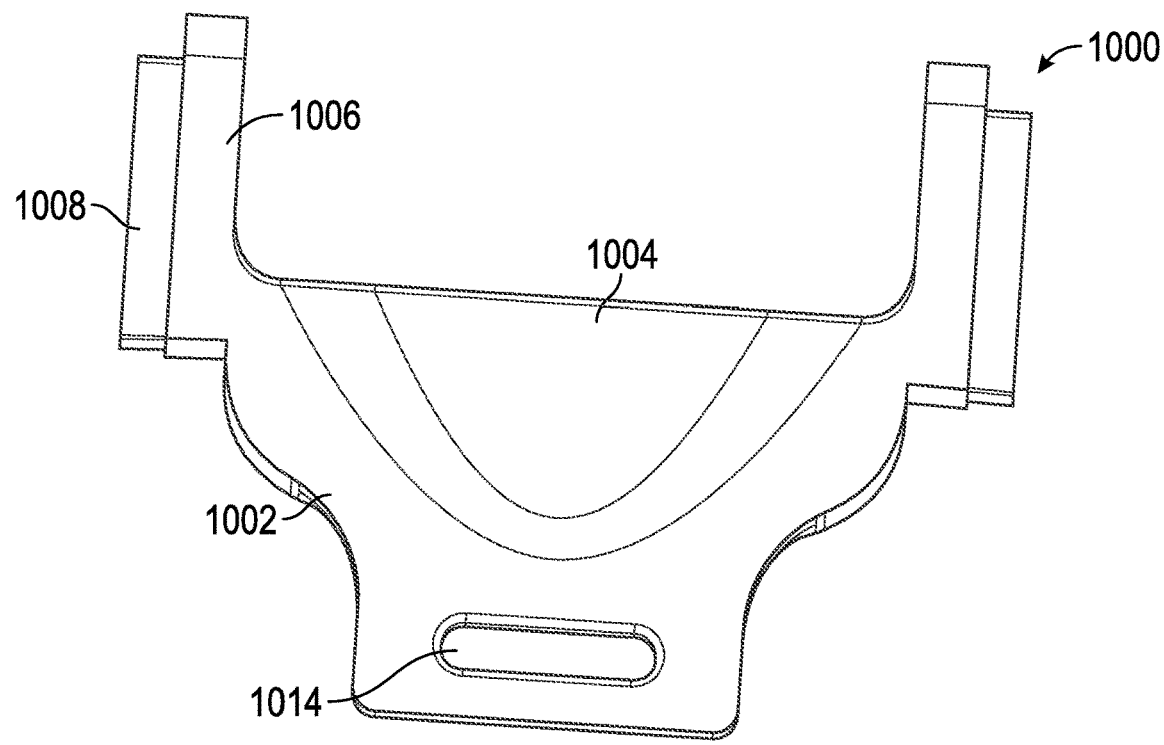
FIG. 11A is a top view of the slide of the speculum of FIG. 1A.
Figure 11B:
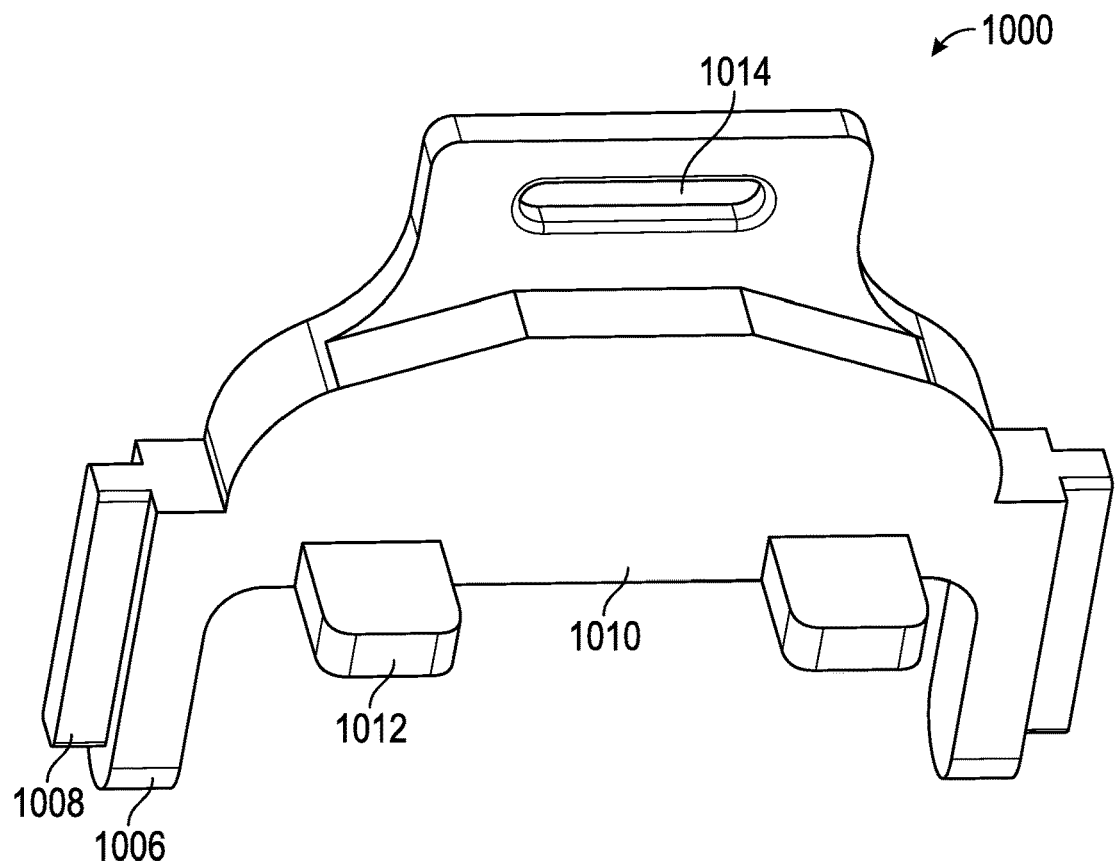
FIG. 11B is a bottom view of the slide of FIG. 10A.

Referring to FIGS. 9-11, the secondary bill assembly 800 of the speculum 100 is shown. The secondary bill assembly 800 includes the right secondary bill 900 (shown in FIG. 10B), the left secondary bill 950 (shown in FIG. 10A), the slide 1000 and dowels 103. The right and left secondary bills 900 and 950 are substantially identical opposites of one another. The right and left secondary bills 900 and 950 includes arms 902 and 952. An exterior of the arms 902 and 952 may have a substantially flat vertical surface 904 and 954 to provide a clear view of the vagina and speculum once inserted by providing support to the side tissue of the vagina. Surfaces 904 and 954 may have a slight curve inward at the tip to provide more comfort when supporting the side tissue of the vagina. The right and left secondary bills 900 and 950 may be sized to fit inside the upper bill 600 and the lower bill 700 when in the closed position. The right and left secondary bills 900 and 950 also include cylindrical connections 906 and 956 that receive dowels 103 to couple the right and left secondary bills 900 and 950 to the handle 400. The right and left secondary bills 900 and 950 also include rotation elements 908 and 958 that limit the rotation of the right and left bills 900 and 950 when the actuation mechanism moves the speculum 100 between the open position and the closed position. The right and left secondary bills 900 and 950 also include horizontal protrusions 910 and 960 that include apertures 912 and 962. The apertures receive dowels 102 that couple the right and left secondary bills 900 and 950 to the slide 1000. The horizontal protrusions 910 and 960 are configured such the lower bill 700 abuts the protrusions 910 and 960, aiding in movement of the slide 1000 and the right and left secondary bills 900 and 950.

The slide 1000 includes a top surface 1002 with a rounded indentation 1004 that matches the curvature of the lower bill 700 to ensure that the slide 1000 does not interfere with the viewing window 610. The slide 1000 includes extensions 1006 on either side with protrusions 1008 that are pressed upon with movement of the upper bill 600, thereby causing slide 1000 to move forward. When the slide 1000 moves forward, dowels 103 held in slot 1014 are pressed forward, thereby rotating horizontal protrusions 910 and 960 and causing the bills 900 and 950 to open. An underside 1010 of the slide 1000 includes stops 1012 that limits movement of the slide 1000 when the actuation mechanism is engaged. The slide 1000 also includes a slot 1014 that receives dowels 102 to couple the slide 1000 to the right and left secondary bills 900 and 950.

Figure 13A:
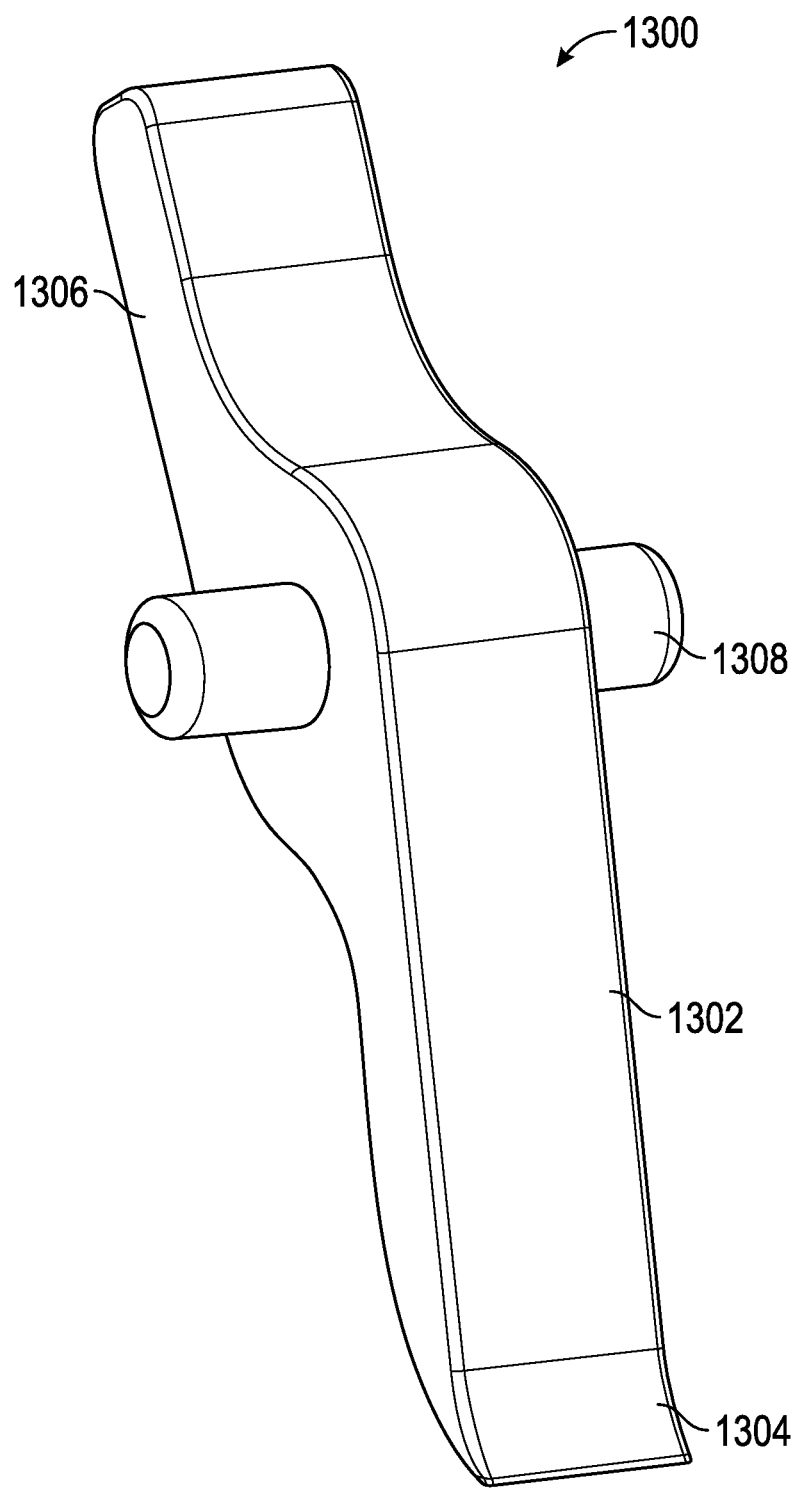
FIG. 13A is a perspective view of a pawl of the speculum of FIG. 1A.
Figure 13B:
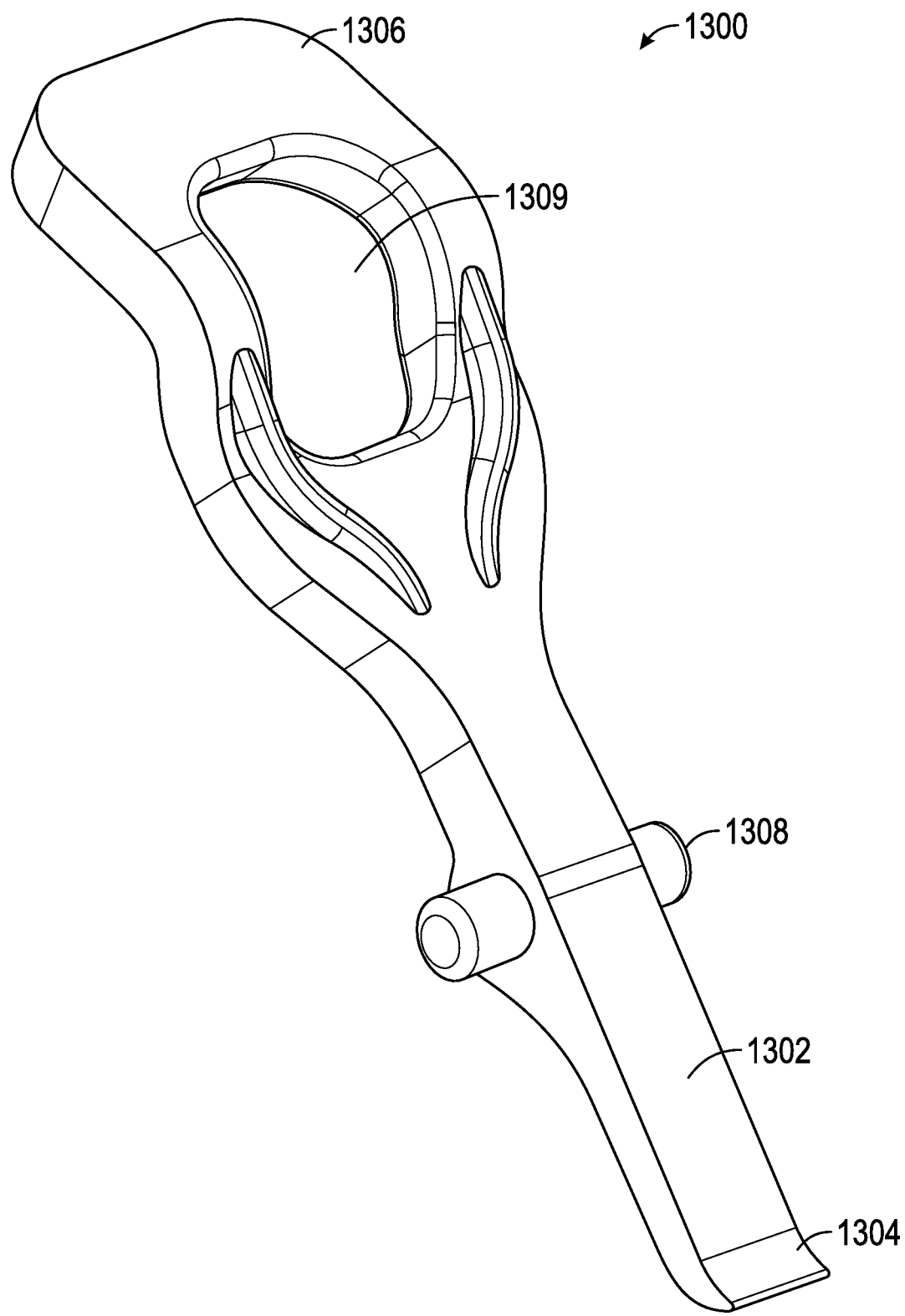
FIG. 13B is a perspective view of a pawl according to a second exemplary embodiment for use with the speculum of FIG. 1A.
Figure 14:
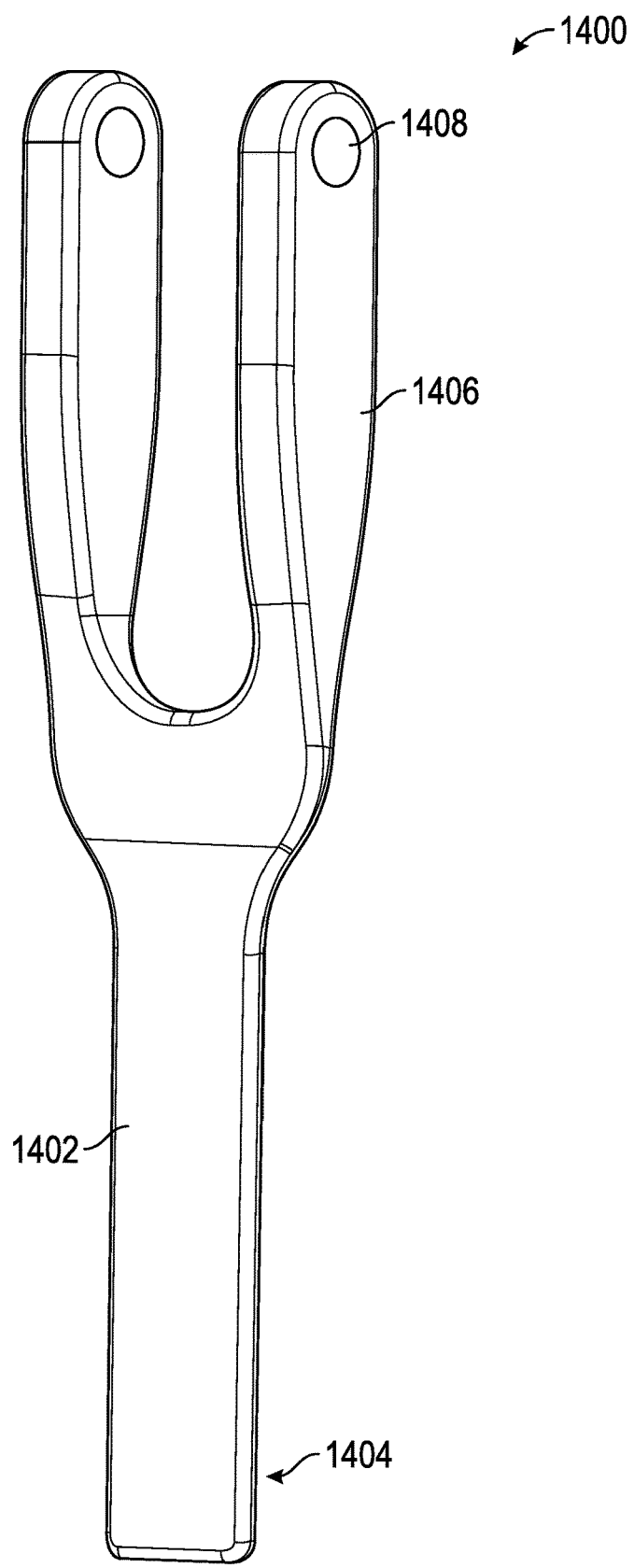
FIG. 14 is a perspective view of a lock strip of the speculum of FIG. 1A.

Referring to FIGS. 12-14, elements of a locking mechanism are shown. The locking mechanism includes the rocker 1100, the pawl 1300 and the lock strip 1400.

Figure 12A:
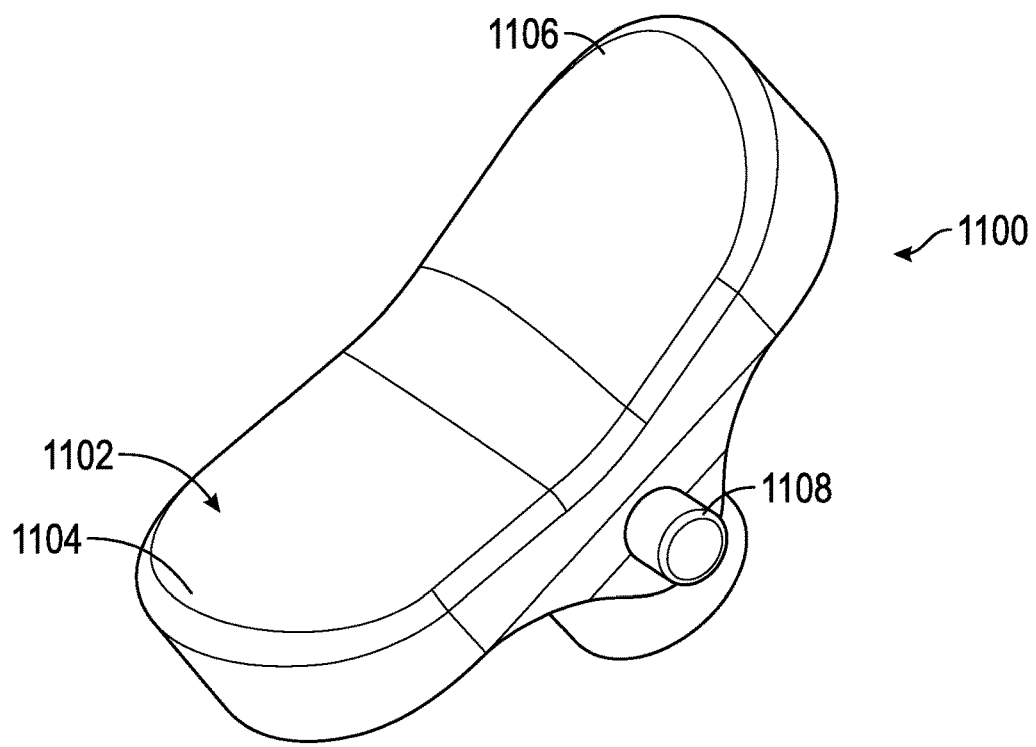
FIG. 12A is a front view of a rocker of the speculum of FIG. 1A.
Figure 12B:
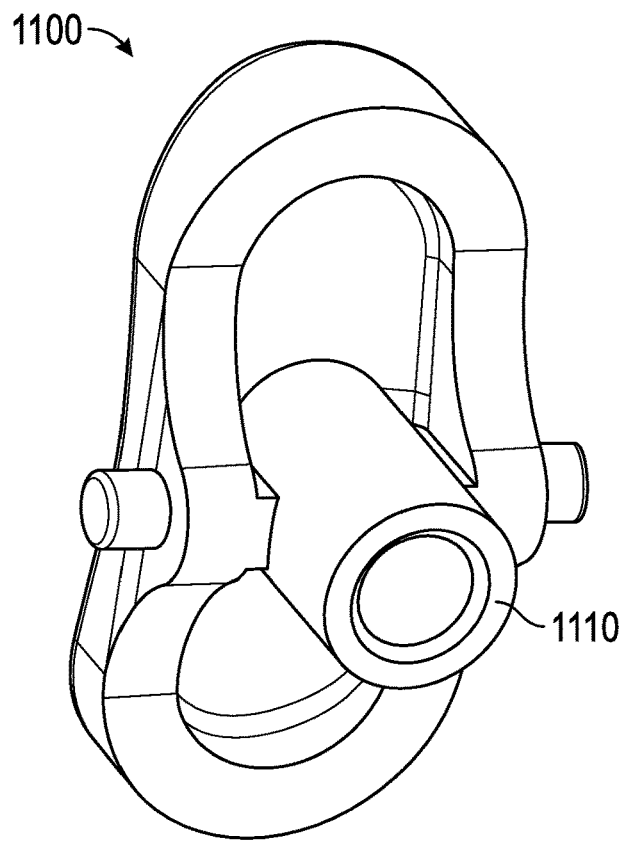
FIG. 12B is a back view of the rocker of FIG. 11A.

Referring to FIGS. 12A and 12B, the rocker 1100 is shown. The rocker 1100 includes an exterior face 1102 that has a curvature such that the rocker 1100 can be moved between a first position and a second position such that a first portion 1104 of the rocker 1100 is substantially flush with the handle 400 in the first position and a second portion 1106 of the rocker 1100 is substantially flush with the handle 400 in the second position. To provide rotation between the first and second position, the rocker 1100 includes knobs 1108 that couple the rocker 1100 to the handle 400. The rocker 1100 further includes a cylindrical housing 1110 that receives the ball plunger 1700 securing the rocker 1100 in place inside the handle 400. In some embodiments, the rocker 1100 is a button that is pushed to lock/unlock the bill portion 200 of the speculum 100 in an open position. Movement of the rocker 1100 between the first position and the second position causes the rocker 1100 to engage or disengage the pawl 1300.

Referring to FIGS. 13A-B, two exemplary embodiments of pawl 1300 are shown. The pawl 1300 rests inside the extensions 424 of the handle 400, with the knobs 1308 on either side resting on the extensions 424. The first portion 1302 of the pawl aligns with a top of the extensions 424 and has a curved end 1304 that is configured to engage with the lock strip 1400. The pawl 1300 also includes a second portion 1306 that abuts the rocker 1100 such that movement of the rocker 1100 either engages or disengages with the pawl 1300, causing rotational movement of the pawl 1300 relative to the lock strip 1400. When the pawl 1300 is engaged with the rocker 1100, the second portion 1306 of the pawl 1300 is moved by the rocker 1100, causing rotation of the pawl 1300 such that the first portion 1302 and specifically the curved end 1304 of the pawl 1300 is positioned away from the lock strip 1400. In this way, when the pawl 1300 is engaged with the rocker 1100, the locking mechanism is in an unlocked configuration. When the pawl 1300 is disengaged, by moving the rocker into the other position, the curved end 1304 of the pawl 1300 may engage with the lock strip 1400. In this way, when the pawl 1300 is disengaged with the rocker 1100, the locking mechanism is in a locked position.

In the embodiment of FIG. 13A, the second portion of the pawl 1306 engages with the bottom portion of the rocker 1100. Thus, in this embodiment, when the bottom portion of the rocker is pressed in, the speculum is unlocked and the speculum is locked when the top portion of the rocker is pressed in. In the embodiment of FIG. 13B, the pawl 1300 has a different design with an aperture 1309 through which the cylindrical housing 1110 and ball plunger 1700 can pass, such that the second portion of the pawl 1306 engages with the top portion of the rocker 1100. Thus, in this embodiment, when the top portion of the rocker is pressed in, the speculum is unlocked and the speculum is locked when the bottom portion of the rocker is pressed in.

Referring to FIG. 14, the lock strip 1400 is shown. The lock strip 1400 includes a flat portion 1402 that extends along the extensions 424 of the handle 400. An underside of the lock strip 1400 includes a plurality of teeth or divots 1404 (not shown) that engage with the curved end 1304 of the pawl 1300. The lock strip 1400 also includes connection mechanisms 1406 with apertures 1408 that receive dowel 102. Dowel 102 extends a width of the handle 400 between two links 1600 with a third link 1600 located in between the connection mechanism 1406. Rotation of the upper bill 600 causes movement of the exterior links 1600, which results in movement of the dowel 102, and ultimately, movement of the lock strip 1400. When the lock strip moves, the divots 1404 to move into position and interact with the curved end 1304 of the pawl 1300. In this way, the locking mechanism locks the bills into an open position when the rocker 1100 is disengaged from the pawl 1300 because the engagement of pawl 1300 with the divots 1404 prevents movement of the lock strip 1400 in a direction that would allow the bills to close. When the rocker 1100 is rotated to the second position, engaging the pawl 1300, the pawl 1300 is moved away from the lock strip 1400, allowing the speculum 100 to return to the closed position by disengaging the curved end 1304 of the pawl 1300 from the divots 1404 of the lock strip 1400. In this unlocked configuration, the speculum can also be opened with minimal resistance or noise. In the locked configuration (e.g., when the rocker 1100 is disengaged from the pawl 1300 and the divots 1404 engage with the curved end 1304), the speculum bills may still open, but will do so with resistance as the curved end 1304 moves from divot 1404 to divot 1404.

Figure 15:
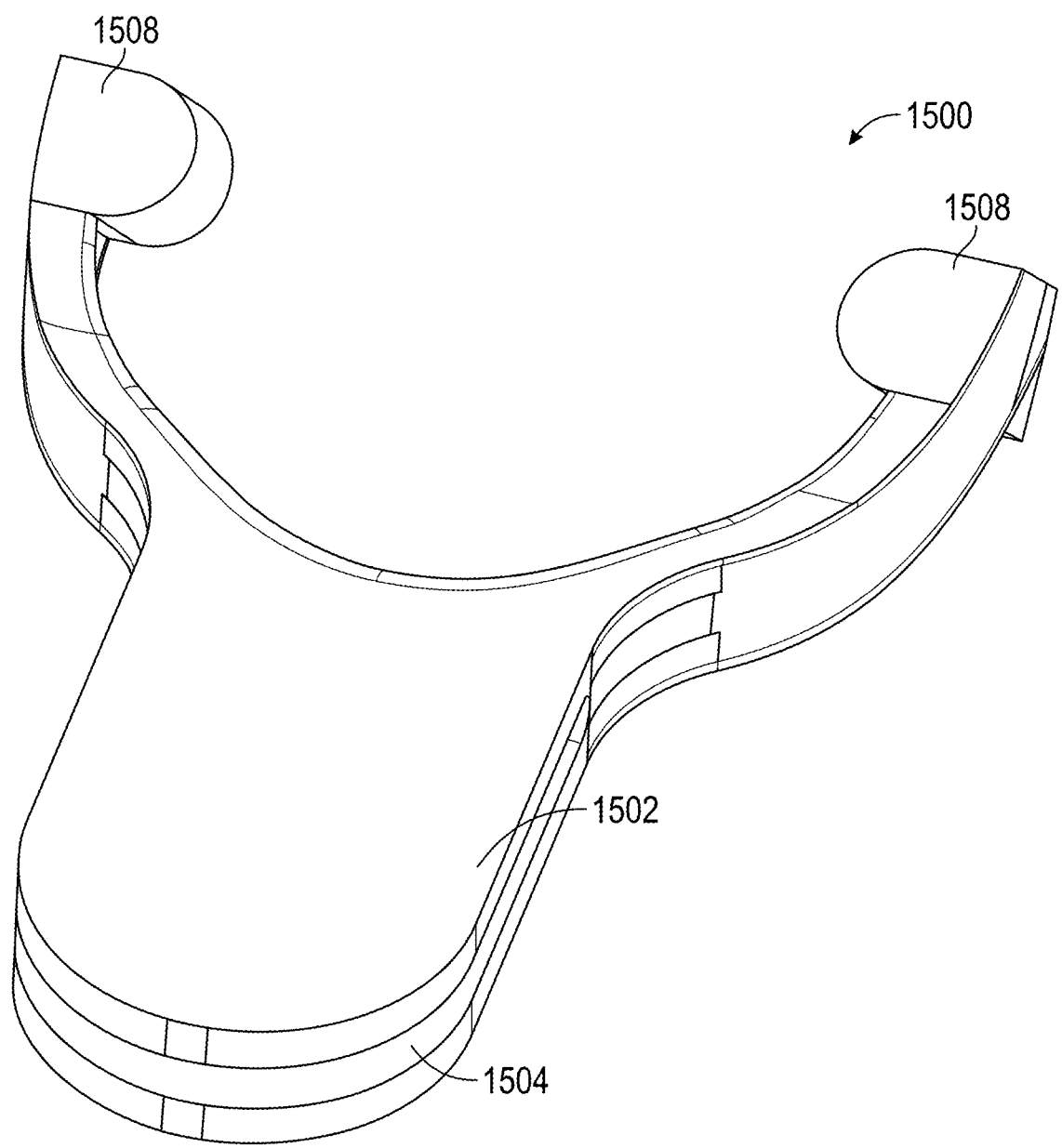
FIG. 15 is a perspective view of an illumination insert of the speculum of FIG. 1A.

In some embodiments, the speculum 100 may include a lighting module, such as lighting module 1500 shown in FIG. 15. The lighting module 1500 may be positioned in the window 610 and held in place by engagement with the window frame 606. The lighting module 1500 includes a base 1502 with a groove 1504 that receives the ridge 614 of the upper bill 600. In other embodiments, the lighting module 1500 may have a snap fit relationship with the window frame 606. In other embodiments, the lighting module may be attached to the window frame 112 using fixation devices (i.e., screws, nails, etc) or adhesive (i.e., tape or glue). The base 1502 is configured to replace the thumb tab 1200, but function in the same way as thumb tab 1200 for providing an actuating mechanism for opening the bills 600 and 700. The lighting module is configured to illuminate the cavity in which the speculum 100 is placed in order to allow better visualization of the cavity and execution of procedures in the cavity. The lighting module 1500 provides one or more illumination elements, such as LEDs. The configuration of the lighting module 1500 provides illumination elements at or near the perimeter of the window 610 at window frame 606, so as not to obstruct the view of the user through the window 610. In the embodiment shown, an illumination element 1508 is positioned on each side of the window frame 606. The illumination element(s) 1508 may alternatively be positioned near any part of the window frame 606. The illumination insert 1500 may be powered by batteries.

The speculum 100 with secondary bills 900 and 950 overcomes the previously described shortcomings of the traditional speculum in a variety of ways. First, the slimmer initial profile (in the insertion position) provides better comfort for the patient. Furthermore, the bill portion 200 may be capable of expanding to a variety of sizes so a single speculum may be appropriate for a number of patients. Also, the bill portion 200 with the secondary bills 900 and 950 provides the side wall support that allows the practitioner better and less impeded visualization and accessibility into the vagina and cervix. Finally, the overall updated design of the speculum 100 lessens anxiety of the patient by eliminating the harsh-looking metal device with sharp edges, and often employing a screw mechanism to hold the bill portion 200 open, with a more streamlined, softer, and overall updated and more modern look and feel.

For the practitioner, the features of the disclosure may reduce fatigue and repetitive stress injury, allow for one-handed opening and locking, allow increased visibility and accessibility, along with many other benefits. For the patients, these features may reduce patient anxiety because they employ quieter mechanism than the traditional designs, significantly reduce the probability of tissues and pubic hair being pinched, and reduce overall anxiety because of the updated look of the opening mechanism and handles.

Some embodiments herein relate to methods of performing obstetric or gynecological procedures utilizing speculum devices and components as described herein described herein. Non-limiting examples of such procedures include pelvic exams, pap smears, insemination, IUD insertion/removal. In some embodiments, the methods can include performing a plurality of such procedures in a given period of time, such as an 8 hour or 24 hour period of time, or any sub period of time therein. Other embodiments relate to methods of reducing hand fatigue or repetitive use injury in a user of a device or handle as described herein.

The foregoing description details certain embodiments of the systems, devices, and methods disclosed herein. It will be appreciated, however, that no matter how detailed the foregoing appears in text, the devices and methods can be practiced in many ways. As is also stated above, it should be noted that the use of particular terminology when describing certain features or aspects of the technology should not be taken to imply that the terminology is being redefined herein to be restricted to including any specific characteristics of the features or aspects of the technology with which that terminology is associated. The scope of the disclosure should therefore be construed in accordance with the appended claims and any equivalents thereof.

It will be appreciated by those skilled in the art that various modifications and changes may be made without departing from the scope of the described technology. Such modifications and changes are intended to fall within the scope of the embodiments, as defined by the appended claims. It will also be appreciated by those of skill in the art that parts included in one embodiment are interchangeable with other embodiments; one or more parts from a depicted embodiment can be included with other depicted embodiments in any combination. For example, any of the various components described herein and/or depicted in the Figures may be combined, interchanged or excluded from other embodiments.

The devices, components, methods and systems described herein can be combined with one or more of the devices, components, methods and systems described in any of U.S. Patent Application entitled "Ergonomically Designed Vaginal Speculum," filed on Dec. 28, 2016, U.S. Patent Application entitled "Insertable Sleeve for Speculum and Use Thereof," filed on Dec. 28, 2016, and U.S. Patent Application entitled "Sleeve for Speculum and Use Thereof," filed on Dec. 28, 2016, each of which is incorporated herein by reference in its entirety.

With respect to the use of any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims are generally intended as "open" terms (e.g., the term "including" should be interpreted as "including but not limited to," the terms "comprising" and "having" should, respectively, be interpreted as "comprising at least" and "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an." In general, "a" and/or "an" should be interpreted to mean "at least one" or "one or more"; the same holds true for the use of definite articles used to introduce claim recitations.

Furthermore, in those instances where a convention analogous to "at least one of A, B, and C, etc." is used, in general, such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

The technology disclosed herein has numerous applications and while particular embodiments of the technology have been described in detail, it will be apparent to those skilled in the art that the disclosed embodiments may be modified given the design considerations discussed herein. Therefore, the foregoing description is to be considered exemplary rather than limiting, and the true scope of the invention is that defined in the following claims.

What is claimed is:

1. A speculum having a narrow profile, allowing for one-handed opening and closing of the speculum, and employing a quiet mechanism for opening and closing the speculum, the speculum comprising:

a handle comprising:
  a distal side configured to accommodate one or more fingers of a user; and
  a proximal side opposite the distal side;
a first bill and a second bill, wherein at least a proximal end portion of the first bill is coupled to an upper portion of the handle, wherein the proximal end portion of the first bill further comprises a window frame defining a viewing window;
a thumb tab coupled to the window frame, wherein a force in a first direction on the thumb tab towards the proximal handle causes the first bill to move relative to the second bill and the handle along a first axis between a closed position and an open position, the thumb tab comprising an exterior surface having a lateral curvature to maintain the viewing window for the user, the thumb tab extending from the viewing window to a lower-most portion of the thumb tab; wherein the distal side of the handle is in contact with the one or more fingers of the user and the proximal side of the handle is accessible to a palm of the user when the thumb tab is depressed by a thumb of the user; and wherein the distal side of the handle is in contact with the one or more fingers of the user and the proximal side of the handle is accessible to the palm of the user and the thumb of the user when the thumb tab is not depressed;
a third bill and a fourth bill, wherein a proximal end portion of the third bill and a proximal end portion of the fourth bill are coupled to the upper portion of the handle and configured to open along a second axis orthogonal to the first axis, the third bill and the fourth bill configured to improve the comfort of a patient and improve a line of sight of the user; and
a locking mechanism configured to lock the speculum in an open position, the locking mechanism comprising:
  a rocker coupled to the handle, the rocker extending between an upper edge and a lower edge opposite the upper edge;
  a lock strip contained in the handle and coupled to at least one of the first bill and the second bill; and
  a pawl coupled to the handle and configured to interact with the lock strip at a first portion of the pawl and with the rocker at a second portion of the pawl,
wherein the lower-most portion of the thumb tab is positioned relative to the handle at a location between the second bill and the lower edge of the rocker when the first bill and the second bill are in the closed position.

2. The speculum of claim 1, wherein the force in the first direction on the thumb tab further causes the third bill and the fourth bill to move between a closed position and an open position.

3. The speculum of claim 2, wherein the third bill and the fourth bill open simultaneously with the first bill and the second bill.

4. The speculum of claim 1, wherein the third bill and the fourth bill are positioned inside of the first bill and the second bill when the first bill and the second bill are in a closed position.

5. The speculum of claim 1, further comprising a sliding surface forming a part of the proximal end portion of the first bill, the sliding surface configured to contact the proximal end portion of each of the third bill and the fourth bill; the sliding surfaces configured to cause outward rotation of the third bill and the fourth bill, thereby causing the third bill and the fourth bill to open.

6. The speculum of claim 1, wherein the speculum is locked and unlocked by a force applied to the rocker.

7. The speculum of claim 1, wherein when the rocker is in a first position, the pawl engages with the lock strip and the speculum is locked in an open position, and wherein when the rocker is in a second position, the pawl is disengaged with the lock strip and the speculum is free to open and close without resistance or noise.

8. The speculum of claim 7, wherein the rocker includes an exterior face that has a curvature such that a first portion of the rocker is flush with the handle in the first position and a second portion of the rocker is flush with the handle in the second position.

9. The speculum of claim 1, wherein the lock strip is configured to engage with the first portion of the pawl and prevent movement of the lock strip relative to the pawl in at least one direction, thereby locking the speculum in an open position.

10. The speculum of claim 1, further comprising an angle between the handle and at least one of the first and the second bill, wherein when the first and the second bill are in a closed position, the angle is in a range of 100 degrees to 180 degrees.

11. The speculum of claim 1, wherein all edges and shape transitions on an outer surface of the handle are rounded.

12. The speculum of claim 1, further comprising a gripping portion.

13. The speculum of claim 12, wherein the gripping portion comprises at least a portion made of a different material than a material of the speculum.

14. The speculum of claim 13, wherein the gripping portion comprises an overmold placed over the handle.

15. The speculum of claim 1, further comprising a lighting module.

16. The speculum of claim 1, wherein the handle has a distal side and a proximal side, the distal side configured to accommodate one or more fingers of a user and the proximal side configured to be accessed by a palm of the user.

17. The speculum of claim 16, wherein the rocker is coupled to the distal side of the handle.

18. The speculum of claim 1, wherein the thumb tab is configured to receive an initial force to cause the first bill to move a first distance relative to the second bill along the first axis; and wherein the thumb tab is configured to receive a subsequent force to cause the first bill to move a second distance relative to the second bill along the first axis.

19. A speculum having a narrow profile, allowing for one-handed opening and closing of the speculum, and employing a quiet mechanism for opening and closing the speculum, the speculum comprising:
  a handle;
  a first bill and a second bill, wherein a proximal end portion of the first bill is coupled to an upper portion of the handle, wherein the proximal end portion of the first bill further comprises a window frame defining a viewing window;
  lateral bills comprising: a third bill and a fourth bill, wherein a proximal end portion of the third bill and a proximal end portion of the fourth bill are coupled to the upper portion of the handle, the third bill and the fourth bill each comprising a flat surface along at least a portion of a side of each of the third bill and the fourth bill, the flat surface providing a clearer view of the vagina and/or cervix of a patient and to support side tissue of the vagina of the patient, the opening of the third bill and the fourth bill configured to improve the comfort of a patient and improve a line of sight of the user;

a thumb tab coupled to the window frame, wherein a force in a first direction on the thumb tab causes the first bill to move relative to the second bill and the handle along a first axis between a closed position and an open position, wherein the force in the first direction on the thumb tab causes the third bill and the fourth bill to move between a closed position and an open position along a second axis orthogonal to the first axis; and a locking mechanism configured to lock or unlock the speculum in response to a force applied to a rocker.

20. The speculum of claim 19, wherein the rocker is a button configured to be pressed to activate the locking mechanism.

\* \* \* \* \*